(12) United States Patent
Guthold et al.

(10) Patent No.: US 8,741,558 B2
(45) Date of Patent: Jun. 3, 2014

(54) COMPOSITIONS, METHODS, AND KITS FOR IDENTIFYING CANDIDATE MOLECULES FROM ENCODED CHEMICAL LIBRARIES

(75) Inventors: Martin Guthold, Pfafftown, NC (US); Jed C. Macosko, Winston-Salem, NC (US)

(73) Assignee: Wake Forest University, Winston-Salem, NC (US)

( * ) Notice: Subject to any disclaimer, the term of this patent is extended or adjusted under 35 U.S.C. 154(b) by 0 days.

(21) Appl. No.: 13/143,433

(22) PCT Filed: Feb. 4, 2010

(86) PCT No.: PCT/US2010/023141
§ 371 (c)(1),
(2), (4) Date: Sep. 29, 2011

(87) PCT Pub. No.: WO2010/091144
PCT Pub. Date: Aug. 12, 2010

(65) Prior Publication Data
US 2012/0021940 A1    Jan. 26, 2012

Related U.S. Application Data

(60) Provisional application No. 61/202,190, filed on Feb. 4, 2009.

(51) Int. Cl.
*C12Q 1/68* (2006.01)
*C12P 19/34* (2006.01)
*C40B 30/02* (2006.01)
*C40B 40/06* (2006.01)

(52) U.S. Cl.
CPC .................................. *C12Q 1/686* (2013.01)
USPC ................. 435/6.1; 435/91.2; 506/9; 506/16

(58) Field of Classification Search
CPC .. C12Q 1/686; C12Q 1/6816; C12N 15/1068; G01N 33/537; G01N 33/57484; C40B 30/04; C40B 40/06
USPC ...................... 506/9, 16, 20, 30; 435/6.1, 91.2
See application file for complete search history.

(56) References Cited

U.S. PATENT DOCUMENTS

| 6,287,765 | B1 | 9/2001 | Cubicciotti et al. |
| 6,391,562 | B2 * | 5/2002 | Kambara et al. ............. 435/6.11 |
| 7,320,864 | B2 * | 1/2008 | Yang ............................. 435/6.1 |
| 8,048,627 | B2 | 11/2011 | Dressman et al. |
| 2002/0164611 | A1 * | 11/2002 | Bamdad et al. ................... 435/6 |

(Continued)

OTHER PUBLICATIONS

Yang X et al. Construction and selection of bead-bound combinatorial oligonucleoside phosphorothioate and phosphorodithioate aptamer libraries designed for rapid PCR-based sequencing. Nucleic Acids Research. 2002; 30(23): e132, 8 pp.

(Continued)

*Primary Examiner* — Narayan Bhat
(74) *Attorney, Agent, or Firm* — Myers Bigel Sibley & Sajovec, P.A.

(57) ABSTRACT

The subject matter relates to relates to a one-bead-one-sequence composition, a library of tagged chemicals comprising a plurality of one-bead-one-sequence compositions, a method for identifying a candidate molecule from a library of tagged chemicals, and a composition produced by a process, all as described herein.

29 Claims, 6 Drawing Sheets

(56) References Cited

U.S. PATENT DOCUMENTS

| | | | |
|---|---|---|---|
| 2003/0228619 A1* | 12/2003 | Needels | 435/6 |
| 2005/0123939 A1 | 6/2005 | Gorenstein et al. | |
| 2007/0065823 A1* | 3/2007 | Dressman et al. | 435/6 |
| 2008/0200340 A1 | 8/2008 | Gorenstein et al. | |
| 2008/0242555 A1 | 10/2008 | Shen et al. | |
| 2008/0255005 A1 | 10/2008 | Gorenstein et al. | |
| 2009/0017022 A1 | 1/2009 | Naworth et al. | |
| 2009/0123922 A1 | 5/2009 | Gorenstein et al. | |

OTHER PUBLICATIONS

Braslavsky I et al. Sequence information can be obtained from single DNA molecules. PNAS. Apr. 1, 2003; 100(7): 3960-3964.

Liu DR et al. Evolutionary principles applied to the discovery and study of functional biological and synthetic molecules. Liu Group Research Summary. Mar. 2006, 10 pp.

Peng L et al. A combined atomic force/fluorescence microscopy technique to select aptamers in a single cycle from a small pool of random oligonucleotides. Microscopy Research and Technique. 2007; 70: 372-381.

Cockroft SL et al. A single-molecule nanopore device detects CAN polymerase activity with single-nucleotide resolution. J. Am. Chem. Soc. 2008 130(3): 818-820.

Mannocci L et al. High-throughput sequencing allows the identification of binding molecules isolated from DNA-encoded chemical libraries. PNAS. Nov. 18, 2008; 105(46): 17670-17675.

Pushkarev D et al. Single-molecule sequencing of an individual human genome. Nature Biotechnology. Sep. 2009; 27(9): 847-852.

Stoddart D et al. Single-nucleotide discrimination in immobilized DNA oligonucleotides with a biological nanopore. PNAS. May 12, 2009; 106(19): 7702-7707.

Gassman NR et al. Selection of bead-displayed, PNA-encoded chemicals. Journal of Molecular Recognition. Sep./Oct. 2010; 23(5): 414-421.

International Search Report and Written Opinion, PCT/US10/23141, mailed Apr. 22, 2010.

Dressman E et al. Transforming single DNA molecules into fluorescent magnetic particles for detection and enumeration of genetic variations. PNAS. Jul. 22, 2003; 100(15): 8817-8822.

* cited by examiner

COMPOSITIONS, METHODS, AND KITS FOR IDENTIFYING CANDIDATE MOLECULES FROM ENCODED CHEMICAL LIBRARIES

RELATED APPLICATIONS

This application is a 35 U.S.C. §371 national phase entry of PCT Application PCT/US2010/023141, filed Feb. 4, 2010, and published in English on Aug. 12, 2010, as International Publication No. WO 2010/091144, and which claims the benefit under 35 U.S.C. §119(e) of U.S. Provisional Patent Application Ser. No. 61/202,190, filed Feb. 4, 2009, the disclosure of each of which is incorporated by reference herein in its entirety.

STATEMENT REGARDING ELECTRONIC FILING OF A SEQUENCE LISTING

A Sequence Listing in ASCII text format, submitted under 37 C.F.R. §1.821, entitled 9151-98 SUBSTITUTE_ST25.txt, 2,732 bytes in size, generated on Mar. 25, 2013 and filed via EFS-Web, is provided in lieu of a paper copy. This Sequence Listing is hereby incorporated by reference into the specification for its disclosures.

BACKGROUND OF THE SUBJECT MATTER

1. Field

The subject matter relates to a one-bead-one-sequence composition, a library of tagged chemicals comprising a plurality of one-bead-one-sequence compositions, a method for identifying a candidate molecule from a library of tagged chemicals, and a composition produced by a process, all as described herein.

2. Background

Pharmaceutical product pipelines and FDA approval rates have weakened dramatically over the past decade. Thus, to aid the discovery of new drugs, Applicants have developed a technology for processing and screening encoded chemical libraries.

State-of-the-Art in Achieving Molecular Recognition.

Currently, specific recognition of molecular targets is primarily achieved using monoclonal antibodies selected by hybridoma technology in which antibody-producing animal cells are hybridized with immortalized myeloma cells. To a much lesser extent, target-specific binding has been demonstrated using peptides selected by phage display or small molecule lead compounds selected by labor-intensive screening methods.

Conceptually, all screening technologies involve finding a "needle in a haystack" by exploiting some property of the needle not found in the rest of the haystack. Often in the prior art, this amounts to a trial-and-error testing of each candidate in the haystack. Ultrahigh-throughput methods allow practical implementation of the trial-and-error screening principle without undue time, expense, effort, and experimentation. However, different screening technologies have been shown to produce very different results in the candidates identified from a given library, and throughput remains inadequate to keep up with available library production capabilities. Therefore, much effort has been devoted to evaluate different screening methods and improve throughput by multiplexing, miniaturizing, and automating.

The three most widely used current methods of target-specific binding (antibodies, peptides, and small molecule pharmacophores) are each associated with their own unique challenges. For example, antibodies are complex proteins with variable glycosylation patterns and microheterogeneity at the antigen binding site. Peptides typically lack this heterogeneity, but share antibodies' sensitivity to extremes of pH and ionic strength. Small molecule lead compounds are chemically well-defined, stable and can be produced with very high purity. However, they are difficult to screen. What is needed is a method to rapidly and sensitively screen promising lead compounds from a large and diverse library of small molecules.

Clonal DNA-bead libraries are a novel improvement over current state-of-the-art products, such as the Clonal Single Molecule Array™ (CSMA) technology developed by Solexa, Inc. In CSMA, single molecules of DNA are attached to a flat surface. The surface is conjugated with PCR primers, and each single molecule of DNA is amplified by PCR to produce ~1000 identical copies, achieving densities of ~10 million clonal clusters per $cm^2$ (1 clonal cluster per 10 $\mu m^2$).

One approach for multiplexing and miniaturizing is to use tiny beads made of different plastics or glasses. These can be functionalized with a range of fluorescent dyes, small molecules and magnetic (or paramagnetic) particles. Beads functionalized in this way can serve both as "handles" and "tags" for small molecule lead compounds and drug candidates during the screening process.

Three primary obstacles stand in the way of using beads to screen small molecule libraries. First, one must find a way to attach enough of the small molecules to the beads in order to generate a detectable signal of the desired functional property. Second, each bead must have only one type of small molecule attached to it so as to avoid attenuating the signal or confounding it with cross-talk. Third, the signal must be processed to convey the identity of the small molecule; when a target-binding bead is detected, its corresponding small molecule is efficiently identified, characterized, and synthesized.

SUMMARY OF THE INVENTION

In the best mode described herein, the subject matter offers solutions to these problems through innovations that create advantageous combinations of two types of libraries: nucleic acid-tagged small molecules and clonal DNA-bead complexes. In this aspect of the subject matter, clonal DNA bead libraries are used to capture, amplify and process PNA or DNA encoded chemicals.

The subject matter—hybridizing tagged candidate chemicals to a monoclonal DNA-bead library—offers a novel and non-obvious solution to all three obstacles, as i) the number of small molecules bound per bead is high, ii) each bead displays only one type of candidate chemical, and iii) the sequenceable molecule of the bead correlates directly with the identity of the candidate chemical.

Applicants have thus developed a technology platform based on simple yet powerful multifunctional beads that will serve as central processing units for screening drug and diagnostic reagent candidates. The subject matter is expected to make a significant contribution to the development of a commercial benchtop system for rapid, automated screening of small molecule libraries. The subject matter comprises compositions and related instrumentation, reagents, assays and kits that enable researchers to rapidly select and characterize small molecule ligands against both established and newly discovered molecular and cellular targets.

A. The subject matter relates to a one-bead-one-sequence composition comprising:
   a) a microscopic bead;
   b) a plurality of identical copies of a single-species, sequenceable molecule, each operably connected to said microscopic bead; and
   c) a tag sequence which is complementary to, and is hybridized to, said sequenceable molecule,
   d) a candidate chemical operably connected to said tag sequence,
   wherein said sequenceable molecule is a unique identifier for its complementary tag sequence,
   and wherein said tag sequence is a unique identifier for its connected candidate chemical.

B. The subject matter further relates to a library of tagged chemicals comprising a plurality of compositions, each composition comprising:
   a) a microscopic bead;
   b) a plurality of identical copies of a single-species, sequenceable molecule, each operably connected to said microscopic bead; and
   c) a tag sequence which is complementary to, and is hybridized to, said sequenceable molecule,
   d) a candidate chemical operably connected to said tag sequence,
   wherein said sequenceable molecule is a unique identifier for its complementary tag sequence,
   and wherein said tag sequence is a unique identifier for its connected candidate chemical.

C. The subject matter additionally relates to a method for identifying a candidate molecule from a library of tagged chemicals, which comprises the steps of:
   a) probing a target molecule with a library of chemical compositions, wherein each composition in the library comprises:
      i) a microscopic bead;
      ii) a plurality of identical copies of a single-species, sequenceable molecule, each operably connected to said microscopic bead; and
      iii) a tag sequence which is complementary to, and is hybridized to, said sequenceable molecule,
      iv) a candidate chemical operably connected to said tag sequence,
      and wherein said tag sequence is unique identifier for its connected candidate chemical;
   b) isolating each composition which binds to said target molecule;
   c) sequencing said sequenceable molecule from each said composition;
   d) identifying, from the standard rules of hybridization, the tag sequence which complements and hybridizes to the identified sequence of said sequenceable molecule; and
   e) identifying, from a database correlating said tag sequence and its connected candidate chemical, the candidate molecule.

D. Finally, the subject matter relates to a composition produced by the process of hybridizing a microscopic-bead-bound sequenceable molecule to a tag sequence that uniquely identifies and is operably connected to a candidate chemical.

DETAILED DESCRIPTION OF EMBODIMENTS

Definitions

Figure 1:
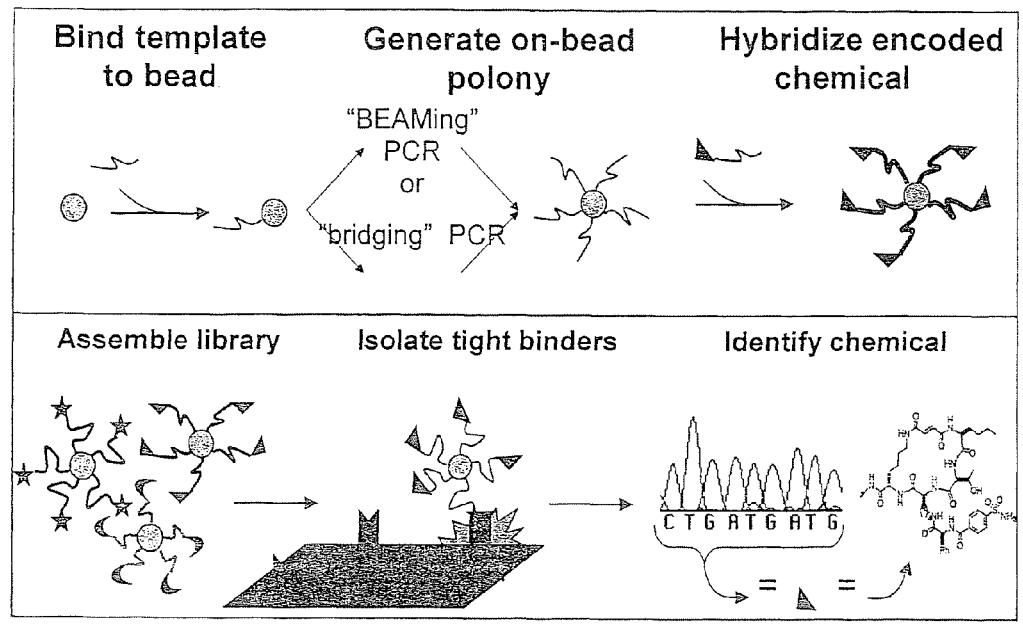
FIG. 1 is two drawings which depicts generating and using libraries. In the top panel: A template strand binds to a bead, is amplified—either with "BEAMing" or "bridging" PCR [1, 5]- and is hybridized to a DNA or PNA encoded chemical. In the bottom panel: A library is screened with surface bound target molecules. DNA on an individual tight-binding bead is amplified and sequenced to decode the identity of the potential drug or diagnostic.

As used herein, the term "microscopic bead" refers to a microparticle support that may be used with the subject matter disclosed, including microparticles made of glass such as controlled pore glass (CPG), highly cross-linked polystyrene, acrylic copolymers, cellulose, nylon, dextran, latex, polyacrolein, and the like, as are well known in the art.

As used herein, the term "sequenceable molecule" refers to a chemical compound or composition for which the primary sequence can be determined. Among the biopolymers that are sequenceable are nucleic acids such as RNA, DNA, modified DNA, PNA, proteins, and polysaccharides, as are well known in the art.

As used herein, the term "tag sequence" refers to a unique chemical sequence which is attached to a candidate chemical, which is complementary to a part of a sequenceable molecule, and which serves to hybridize to a sequenceable molecule. In some embodiments the tag sequence is a nucleic acid having, from 5' to 3', the general formula A-B-C, where A is an optional primer segment, B is a variable segment, and C is an optional primer segment. Primer segments A and C are, in general, from 8 or 10 nucleic acids in length up to 100 or 200 nucleic acids in length, or more. Variable segment B is, in general, from 10 or 20 nucleic acids in length up to 1000 nucleic acids in length, or more. While each variable segment is unique for the corresponding connected candidate chemical, primer segments are preferably the same for all connected different candidate chemicals, so that each unique identifier can be amplified by the same amplification reaction. Inactive segments may be included if desired. In some embodiments A and C are both present and are corresponding forward and reverse primer segments; in some embodiments one or the other of A and B is omitted and only a single primer segment is included.

As used herein, the term "candidate chemical" refers to a chemical compound which is used in the context of a "test compound" or a "drug candidate compound" used in connection with the assays described herein. Such chemicals comprise organic or inorganic compounds, derived synthetically or from natural sources. Candidate chemicals are, in some embodiments, preferably small molecules.

"Small molecule" as used herein is defined as a molecule with a molecular weight that is less than 10 kD, typically less than 2 kD, and preferably less than 1 kD. Small molecules typically have a molecular weight of 100, 200, or 300 daltons or more. Small molecules include, but are not limited to, inorganic molecules, organic molecules (e.g., peptides, glycopeptides, amido peptides, etc.) organic molecules containing an inorganic component, molecules comprising a radioactive atom, synthetic molecules, peptide mimetics, and antibody mimetics. As a therapeutic, a small molecule may be more permeable to cells, less susceptible to degradation, and less apt to elicit an immune response than large molecules. Small molecules, such as peptide mimetics of antibodies and cytokines, as well as small molecule toxins are described (see, e.g., Oft et al., US Pat. Appln. Publication No. 20100003251 (Jan. 7, 2010); see also U.S. Pat. No. 6,326,482. An extensive list of example compounds that may be small molecules or candidate chemicals used in the inventions described herein is set forth in W. Hunter, et al., US Patent Application Publication No. 20050181977 (Published Aug. 18, 2005) (see paragraphs 0065 through 0387 therein), the disclosure of which is incorporated by reference herein in its entirety.

As used herein, the term "directly-sequenceable" refers to a chemical compound or composition for which the primary sequence can be determined without amplification prior to sequencing.

As used herein, the term "operably connected" refers to a attachment of one molecule to another in such a configuration that the relevant function(s) of each molecule operably connected is/are not destroyed. For example, a sequenceable molecule operably connected to a microscopic bead must retain its ability to hybridize to its complementary tag molecule. Similarly, for a tag molecule operably connected to a candidate chemical, the tag molecule must retain its ability to hybridize to its complementary sequenceable molecule, while the candidate chemical must retain its ability to bind its target molecule. In a preferred embodiment, "operably connected" refers to a covalent linkage. However, non-covalent linkages, such as chelation, antigen-antibody complexes, and other types of bonding may also be utilized.

A nucleic acid (NA) sequenceable molecule may be attached to a microscopic bead in any manner known in the art. Numerous methods exist in the art for attaching NA to a solid support such as a microscopic bead. In one aspect, covalent chemical attachment of the NA to the bead can be accomplished by using standard coupling agents, such as water-soluble carbodiimide, to link the 5'-phosphate on the NA to amine-coated capture beads through a phosphoamidate bond.

Another alternative is to first couple specific oligonucleotide linkers to the bead using similar chemistry, and to then use an appropriate ligase to link the NA to the linker on the bead.

Oligonucleotide linkers can be employed which specifically hybridize to unique sequences at the end of the DNA fragment, such as the overlapping end from a restriction enzyme site or the "sticky ends" of bacteriophage lambda based cloning vectors, but blunt-end ligations can also be used beneficially.

Other linkage chemistries to join an oligonucleotide to a bead include the use of N-hydroxysuccinamide (NHS) and its derivatives. Homopolymer linkers may also find utility in certain applications. By employing oligo-dT coupled to the bead, it is possible to hybridize to the poly-A tail found in mRNA as a means for directly sequencing mRNA isolated from cells.

Yet another method for coupling NA to beads employs specific ligands attached to the end of the NA to link to ligand-binding molecules attached to the bead. For example, a terminal transferase can be used to incorporate such a ligand onto the end of the DNA, oligonucleotide linkers already containing an appropriate ligand can be ligated to the DNA, or oligonucleotides capable of forming a stable triple-helix with a target duplex DNA can be synthesized to incorporate an appropriate ligand (see, e.g., Smith et al., "Direct Mechanical Measurements of the Elasticity of Single DNA Molecules by Using Magnetic Beads," Science 258:1122-1126, 1992, which is incorporated herein by reference).

In one particular embodiment in which the DNA contains the appropriate single-stranded telomeric recognition site, telomere terminal transferase (Greider et al., 1987, Cell 51:887-898, which is incorporated herein by reference) can be used to incorporate a biotinylated nucleotide at the 3' end of the DNA which can then be bound to avidin immobilized on the bead. In this embodiment, a 5' to 3' exonuclease would then be used for sequencing, since the 3' end would be the "tethered" end.

In yet another embodiment, calf thymus terminal transferase (Kato et al., 1967, J. Biol. Chem. 242:2780, which is incorporated herein by reference) can be used to incorporate a ligand-linked nucleotide onto the 3' end of any DNA molecule with a free 3' hydroxyl group. U.S. Pat. No. 6,420,112 also describes a method for attaching nucleic acids, such as DNA, to microscopic beads or other support structures using a terminal transferase.

In still another approach, a DNA-binding protein can be coupled to the bead by chemistries well known in the art and in such a fashion that the DNA-binding site is unperturbed. DNA containing the recognition sequence for the DNA-binding protein can thereby be coupled to the bead.

As used herein, the term "ligand-binding partner pair" refers to a pair of molecules which exhibit strong affinity and specificity. Such pairs include, but are not limited to, biotin-avidin/streptavidin/neutravidin, or various antibody/antigen pairs such as digoxygenin-anti digoxygenin.

As used herein, the term "unique identifier" refers to any identifier which is guaranteed to be unique among all identifiers used for a given set of objects and specific purpose. In particular, for a sequenceable molecule, its complementary tag molecule, and the candidate chemical operably connected to the tag molecule, there is a unique and unambiguous relationship between the molecules in that group.

As used herein, the term "PNA" refers to Peptide nucleic acid. PNA is an artificially synthesized polymer similar to DNA or RNA. PNA is not known to occur naturally. The PNA backbone is composed of repeating N-(2-aminoethyl)-glycine units linked by peptide bonds, unlike DNA and RNA, which, respectively, have a deoxyribose and ribose sugar backbones. Purine and pyrimidine bases are linked to the PNA backbone by methylene carbonyl bonds. PNA is an effective structural mimic of DNA and RNA, and PNA oligomers are able to form very stable duplex structures with Watson-Crick complementary DNA, RNA, or PNA oligomers.

As used herein, the term "modified DNA" refers to a DNA molecule which has been chemically modified, while retaining the ability to form very stable duplex structures by Watson-Crick complementary with other DNA, modified DNA, RNA, or PNA oligomers. Examples of modified DNA include molecules modified at the base moiety, sugar moiety or phosphate backbone to improve, e.g., the stability and/or hybridization properties of the molecule.

For example, the deoxyribose phosphate backbone of the nucleic acid molecules can be modified to generate peptide nucleic acids, glycerol nucleic acids, locked nucleic acids, threose nucleic acid, and phosphorodiamidate morpholino oligos.

Examples of modified nucleotides which can be used to generate a modified nucleic acid include base-boronated dinucleotides, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine.

As used herein, the term "polymerase chain reaction" or "PCR" refers broadly to a process for amplifying DNA by in vitro enzymatic replication using a DNA polymerase, usually a heat-stable DNA polymerase such as Taq polymerase; deoxynucleoside triphosphates (dNTPs); and oligonucleotide primers. The DNA generated in each PCR cycle is used as a template in the next cycle, and the DNA template is exponentially amplified.

There are many variants of PCR well known in the art. One of the most common is "reverse-transcriptase polymerase chain reaction" or "RT-PCR", a common method used to amplify RNA. In RT-PCR, use of reverse transcriptase, an enzyme that converts RNA into cDNA, precedes PCR. Among the PCR variants, the following are most relevant to the disclosed subject matter:

Multiplex-PCR can involve up to a dozen pairs of primers acting independently. This modification is used to simultaneously analyze multiple targets in a sample.

Isothermal amplification is an approach to amplify nucleic acid that uses only a single temperature incubation, whereas regular PCR uses three different temperatures for primer annealing, primer extension and denaturation.

Asymmetric PCR is used to preferentially amplify one strand of the target DNA, and is used where having only one of the two complementary strands of the product is advantageous. PCR is carried out as usual, but with a limiting amount of one of the primers. When it becomes depleted, continued replication leads to an arithmetic increase in extension of the other primer and its corresponding DNA. A recent modification on this process is known as Linear-After-The-Exponential-PCR (or LATE-PCR).

Hot-start/cold-finish PCR is achieved with hybrid polymerases that are inactive at ambient temperature and are only activated at elevated temperatures. In Touchdown PCR, the temperature used to anneal the primers is gradually decreased in later cycles. The initial higher annealing temperature, 3-5° C. above the standard melting temperature of the primers used, leads to greater specificity for primer binding, while lower temperatures permit more efficient amplification at the end of the reaction.

All of the PCR variants enumerated herein, and others not explicitly identified, are understood to involve routine optimization of the basic PCR process, and are intended to be within the broad scope of the term "PCR" as used herein. So long as a particular technique serves the purpose of amplifying DNA by in vitro enzymatic replication using a DNA polymerase, deoxynucleoside triphosphates, and oligonucleotide primers, it is considered within the scope of the present claims.

As used herein, the term "library of tagged chemicals" refers to a plurality of candidate chemicals, the corresponding tag sequence of each candidate chemical, and the sequenceable molecule complementary to each tag sequence.

As used herein, the term "highly stringent conditions" refers to the conditions under which a sequenceable molecule will hybridize to its tag sequence, to the exclusion of other sequences. This is also known in the art as homologous probing. Highly stringent conditions are sequence-dependent and will be different in different circumstances. By controlling the stringency of the hybridization and/or washing conditions, a tag sequences and its corresponding candidate chemical can be identified which is 100% complementary to the sequenceable molecule. Generally, highly stringent conditions are selected to be less than about 5° C. lower than the thermal melting point for the specific sequence and its complement at a defined ionic strength, wash conditions, pH, and percentage of destabilizing agent(s) such as formamide. Stringency conditions are known in the art and can be found, for example, in Current Protocols in Molecular Biology (John Wiley & Sons, New York (1989), 6.3.1-6.3.6 which is incorporated herein by reference. Further, an extensive guide to the hybridization of nucleic acids is found in Tijssen, Laboratory Techniques in Biochemistry and Molecular Biology—Hybridization with Nucleic Acid Probes, Part I, Chapter "Overview of principles of hybridization and the strategy of nucleic acid probe assays", Elsevier, New York (1993); and Current Protocols in Molecular Biology, Chapter 2, Ausubel, et al., Eds., Greene Publishing and Wiley-Inter science, New York (1995), which are incorporated herein by reference.

As used herein, the term "target molecule" refers to a molecule which is the target for testing for a desired interaction with one or more candidate chemical(s). The term "stringent" as used here refers to hybridization conditions that are commonly understood in the art to define the commodities of the hybridization procedure. Stringency conditions can be low, high or medium, as those terms are commonly know in the art and well recognized by one of ordinary skill. High stringency hybridization conditions that will permit homologous nucleotide sequences to hybridize to a nucleotide sequence as given herein are well known in the art. As one example, hybridization of such sequences to the nucleic acid molecules disclosed herein can be carried out in 25% formamide, 5×SSC, 5×Denhardt's solution and 5% dextran sulfate at 42 degrees C., with wash conditions of 25% formamide, 5×SSC and 0.1% SDS at 42 degrees C., to allow hybridization of sequences of about 60% homology. Another example includes hybridization conditions of 6×SSC, 0.1% SDS at about 45 degrees C., followed by wash conditions of 0.2× SSC, 0.1% SDS at 50-65 degrees C., at, for example, about 60, 70, 80 or 90 percent homology, or more. Another example of stringent conditions is represented by a wash stringency of 0.3 M NaCl, 0.03M sodium citrate, 0.1% SDS at 60-70 degrees C. using a standard hybridization assay (see SAMBROOK et al., EDS., MOLECULAR CLONING: A LABORATORY MANUAL 2d ed. (Cold Spring Harbor, N.Y. 1989, the entire contents of which are incorporated by reference herein). In various embodiments, stringent conditions can include, for example, highly stringent (i.e., high stringency) conditions (e.g., hybridization to filter-bound DNA in 0.5 M NaHPO$_4$, 7% sodium dodecyl sulfate (SDS), 1 mM EDTA at 65 degrees C., and washing in 0.1×SSC/0.1% SDS at 68 degrees C.), and/or moderately stringent (i.e., medium stringency) conditions (e.g., washing in 0.2×SSC/0.1% SDS at 42 degrees C. See, e.g., U.S. Pat. No. 7,645,602).

Subject Matter

Pharmaceutical product pipelines and FDA approval rates have weakened dramatically over the past decade. Thus, to aid the discovery of new drugs, Applicants have developed a technology for processing and screening encoded chemical libraries. Molecular targets for diseases are discovered at a rapid pace, but finding chemicals that bind these targets-even with high throughput screening-is slow, and the majority of candidates fail physicochemical and biological requirements. This situation would be improved by ultra-high-throughput screening via encoded chemical libraries, which could be achieved via a method that would quickly and sensitively screen and identify the encoded chemicals. The subject matter is at the core of such a method; it serves as –a central processing unit that amplifies and reads out a unique-identifier molecule at the level of single nanoscopic beads.

The subject matter includes bead-based compositions, reagent kits, and microfluidic systems which are used discover new drug leads and diagnostic reagents, which are capable of boosting screening sensitivity and throughput well beyond current fluorescence methods and iterative amplification-and-selection techniques.

The subject matter described in this application will provide biochemists who develop nucleic acid-tagged small molecule libraries with a sensitive tool for screening lead compounds and drug candidates. This tool promises to be orders of magnitude more sensitive than state-of-the-art encoded small molecule screening techniques, with a minimum detection concentration of about 10 compared to conventional detection of about $10^{-11}$ M (see, e.g., Urbina, et al., Chembiochem, 2006, 7(11):1790-1797). Thus, the subject matter is expected to be able to screen tagged small molecule libraries at near single-molecule sensitivity. Screening such libraries at such high sensitivity would significantly enhance researchers' ability to discover synthetic small molecules with functional properties. Similarly, the subject matter is expected to enhance the ability to detect active small molecules in PNA-encoded libraries, which is expected to expand the scope of problems that can be targeted. It is expected that the subject matter will provide the capability for screening methods which combine the broad diversity of small molecule libraries with the tracking and identification benefits of nucleic acid tagging.

Further, the subject matter ultimately is expected to improve human health, for example identifying and isolating new drugs for cancer patients, for whom safe and effective therapies are currently lacking. It is currently expected that Applicants' first therapeutic objective is to screen chemical libraries for interaction with clinically-relevant targets such as ErbB-2 or ErbB-3, which are epidermal growth factor receptors known to be over-expressed on cell surfaces of several types of cancer, including carcinomas of the breast, bladder, colon, pancreas, ovary and prostate.

Particular examples of other targets for screening include, but are not limited to; for breast cancer, wherein optionally the target gene comprises BRCA and/or Her-2/neu; for Burkitt's Lymphoma, wherein optionally the target gene comprises Myc; for prostate cancer, wherein optionally the target gene comprises c-Myc; for colon cancer, wherein optionally the target gene comprises MSH; for lung cancer, wherein optionally the target gene comprises EGFR (ErbB-1), Her 2/neu (ErbB-2), Her 3 (ErbB-3) and/or Her 4 (ErbB-4); for Chronic Myeloid Leukemia (CML), wherein optionally the target gene comprises BCR-ABL; and/or, for malignant melanoma, wherein optionally the target gene comprises CDKN2 and/or BCL-2. In one aspect, methods of the invention can comprise identifying a compound therapeutic wherein the target gene comprises PKA, VEGFR, VEGFR2, PDGF and/or PGGFR. See, e.g., US Patent Application Publication No. 2007/0154906 at paragraph 39 therein.

Thus, the subject matter relates to a one-bead-one-sequence composition, a library of tagged chemicals comprising a plurality of one-bead-one-sequence compositions, a method for identifying a candidate molecule from a library of tagged chemicals, and a composition produced by a process, all as described herein.

Compositions

The subject matter relates to a one-bead-one-sequence composition comprising:

a) a microscopic bead;

b) a plurality (e.g., 2, 50, or 100, up to $10^{11}$ or $10^{12}$ or more) of identical copies of a single-species, sequenceable molecule (e.g., a nucleic acid), each operably connected to said microscopic bead; and c) a tag sequence which is complementary to, and is hybridized to, said sequenceable molecule, d) a candidate chemical operably connected to said tag sequence, wherein said sequenceable molecule is a unique identifier for its complementary tag sequence, and wherein said tag sequence is a unique identifier for its connected candidate chemical.

In one aspect of the subject matter, said candidate chemical is produced by template-directed synthesis using said tag sequence as the template.

In another aspect of the subject matter, said tag sequence is selected from the group consisting of DNA, modified DNA, RNA, and PNA. In this aspect, PNA-tagged or DNA-tagged small molecule libraries are used to determine the identity of promising lead compounds using the sequence information of the nucleic acid tag (see, e.g., Gartner, et al., Science, 2004, 305(5690):1601-1605 and Harris, et al., Chemistry—a European Journal, 2005, 11(23):6792-6801). One advantage of PNA is that it is more stable during synthesis of the small molecule library and therefore offers more options for plausible drug candidates. On the other hand, DNA tags are attractive because the sequence information can be directly amplified by PCR.

In a preferred embodiment, said tag sequence is DNA.

In one aspect of the subject matter, said tag sequence is operably connected to said candidate chemical by a covalent bond.

In an alternate aspect of the subject matter, said tag sequence is bound to said candidate chemical during or after the synthesis of said candidate chemical, in some embodiment provided that said candidate chemical is not produced by template-directed synthesis using said tag sequence as the template.

In a preferred embodiment of this aspect, said tag sequence is selected from the group consisting of DNA, modified DNA, RNA, and PNA.

In a further preferred embodiment, said tag sequence is PNA.

In another preferred embodiment, said tag sequence is DNA.

In another aspect of the subject matter, said tag sequence is operably connected to said candidate chemical by a covalent bond.

In yet another aspect of the subject matter, said hybridization of said tag sequence and said sequenceable molecule occurs only under stringent or highly stringent conditions.

In a further aspect of the subject matter, said sequenceable molecule is a nucleic acid, e.g., selected from the group consisting of DNA, modified DNA, RNA, and PNA.

In a preferred embodiment, said sequenceable molecule is DNA.

In a related aspect, the subject matter combines strategies: it couples PNA's organic-synthesis-compatibility, which is important during chemical synthesis of a candidate chemical, with DNA's PCR-detection-compatibility via its novel monoclonal bead hybridization method, which is important for efficiently identifying the candidate chemical.

In yet another aspect of the subject matter, said sequenceable molecule is operably connected to said microscopic bead by a ligand-binding partner pair.

In a preferred embodiment, said ligand-binding partner pair is (a) biotin and (b) one or more biotin ligands selected from the group consisting of avidin, streptavidin, and neutravidin.

In a further aspect of the subject matter, the process for sequencing the sequenceable molecule is selected from the group consisting of polymerase chain reaction, reverse-transcriptase polymerase chain reaction, or modified polymerase chain reaction (e.g., e.g., one-directional PCR, quantitative PCR, isothermal amplification and the like).

In a preferred embodiment, the process for amplifying the sequenceable molecule is polymerase chain reaction.

In one aspect of the subject matter, said microscopic bead is between 10 nanometers and 30 microns in diameter.

In a preferred embodiment, said microscopic bead is between 100 nanometers and 1 micron in diameter.

In another aspect of the subject matter, said microscopic bead comprises glass, or an organic polymer, e.g. plastic, acrylic copolymers, cellulose, nylon, dextran, latex, and polyacrolein.

In a preferred embodiment, said microscopic plastic bead comprises polystyrene.

Applicants have demonstrated the subject matter by successfully attaching DNA to two sets of beads, such that the experimental bead set hybridized to a particular PNA strand and the negative control did not. The highly stringent conditions for PNA to hybridize to the DNA bound to 160 nm polystyrene beads were optimized for 40% formamide at 50° C., followed by spinning at 20,000 g for 10 min and resuspension in pH 8.8 buffer containing 10 mM Tris 50 mM KCl, 0.01% Triton X-100, 3 mM $MgCl_2$, and 8% glycerol. The bead-bound DNA was amplified by PCR, and the amplification products from the bead sets were determined by gel electrophoresis after a restriction enzyme digest with XcmI and Tsp45I (New England BioLabs Inc., Ipswich, Mass.), and also by DNA sequencing.

The subject matter further relates to a library of tagged chemicals comprising a plurality (e.g., 2, 50, 100, 1,000 up to $10^8$, $10^{12}$ or $10^{15}$ or more) of compositions, each composition comprising:

a) a microscopic bead;

b) a plurality (e.g., 2, 50, or 100, up to $10^{11}$ or $10^{12}$ or more) of identical copies of a single-species, sequenceable molecule, each operably connected to said microscopic bead; and c) a tag sequence which is complementary to, and is hybridized to, said sequenceable molecule, d) a candidate chemical operably connected to said tag sequence, wherein said sequenceable molecule is a unique identifier for its complementary tag sequence, and wherein said tag sequence is a unique identifier for its connected candidate chemical.

In one aspect of the subject matter, each said composition comprises a candidate chemical produced by template-directed synthesis using said tag sequence as the template.

The best mode of practicing the subject matter is shown in FIG. 1, in which a microscopic (100-200 nm), optionally fluorescent, bead is functionalized with many copies of the same single-stranded DNA template. The ends of these templates share identical PCR primer regions, but the middle region, in between the two primer regions, is unique to each DNA template. The primer regions are used to amplify the original template into a "polony"—a monoclonal colony of polymerized DNA strands—via PCR methods (see, e.g., Dressman, et al., Proceedings of the National Academy of Sciences, 2003, 100(15):8817-8822 and Bing, et al., Bridge Amplification: A Solid Phase PCR System for the Amplification and Detection of Allelic Differences in Single Copy Genes, http://www.promega.com/geneticidproc/ussymp7proc/0726.html, 1996, Seventh International Symposium on Human Identification (Genetic Identity Conference Proceedings), each of which is incorporated by reference herein). In the top panel of FIG. 1, a template strand binds to a bead, is amplified—either with "BEAMing" or "bridging" PCR—and is hybridized to a DNA or PNA encoded chemical. In the bottom panel of FIG. 1, a library is screened with surface bound target molecules. DNA on an individual tight-binding bead is amplified and sequenced to decode the identity of the potential drug or diagnostic.

The unique middle region, referred to herein as a DNA-"sequenceable molecule", hybridizes to a DNA-encoded or PNA-encoded chemical. Since each bead is a monoclonal polony, the subject matter provides for only one type of chemical hybridize to each bead—a key innovation of the subject matter. Thus, by isolating individual beads that bind tightly to target molecules, and by amplifying and sequencing their unique middle hybridizing regions, the attached encoded molecules (which cause the tight-binding) can be identified, as shown in the bottom panel of FIG. 1. A library comprising a plurality of beads thus serves as a highly efficient clearinghouse for chemical library processing. The one-bead-one-sequence relationship of such nanoscopic laboratories allows only identically encoded small molecules to self-assemble, creating synergy that enhances their functional properties and detectability.

Figure 2:
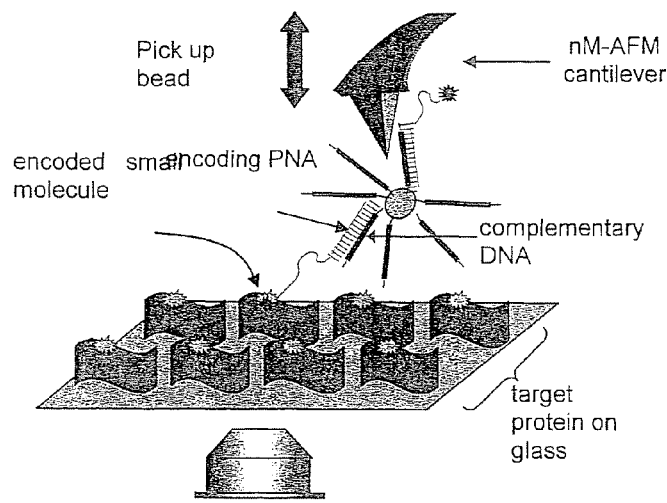
FIG. 2 is a drawing which depicts a nanoManipulator-atomic force microscope (nM-AFM) bead pick-up schematic. The sharp tip of the nM-AFM cantilever is centered, via fluorescence imaging, above a bound bead. The tip is lowered to spear the bead, and then retracted to pick it up.

In one embodiment, Biotin was used as a model PNA-encoded small molecule, and streptavidin was used as the target (data not shown). Initially, the two bead sets were kept separate and allowed to interact in two separate reactions with immobilized streptavidin targets on a glass surface. The PNA complementary DNA bead bound this surface more efficiently than the non-complementary beads, which demonstrated that the PNA was properly hybridized and that its attached biotin was free to interact with the surface. Subsequently, Applicants mixed the two bead sets together and used the tip of their nanoManipulator atomic force microscope (nM-AFM) to pick up the tightly bound beads for PCR amplification. The bead pick up schematic is shown in FIG. 2.

Applicants have demonstrated superb control over two modes of bead pick-up: AFM (peng et al) and micropipetting (Gassman et al). Beads have been picked up by spearing the bead with a sharp AFM tip and lifting off the surface. One skilled in the art can observe the bead when it is attached to the tip and transferred to a tube for further DNA amplification and sequencing. Alternatively, a bead has been picked up and deposited for sequencing by vacuuming the bead onto a micropipette. Again, a skilled operator has excellent control over this process as well.

Methods

The subject matter relates to a method for identifying a candidate molecule from a library of tagged chemicals, which comprises the steps of:

a) probing a target molecule with a library of chemical compositions, wherein each composition in the library comprises:

i) a microscopic bead;
ii) a plurality of identical copies of a single-species, sequenceable molecule, each operably connected to said microscopic bead; and
iii) a tag sequence which is complementary to, and is hybridized to, said sequenceable molecule,
iv) a candidate chemical operably connected to said tag sequence,
and wherein said tag sequence is a unique identifier for its connected candidate chemical;

b) isolating each composition which binds to said target molecule;

c) sequencing said sequenceable molecule from each said composition;

d) identifying, from the standard rules of hybridization, the tag sequence which complements and hybridizes to the identified sequence of said sequenceable molecule; and e) identifying, from a database correlating said tag sequence and its connected candidate chemical, the candidate chemical.

In another aspect, the method above further comprises, between steps (b) and (c), the additional steps of:

i) isolating the single-species, sequenceable molecule from each said composition which binds to said target molecule; and ii) amplifying said sequenceable molecule.

Probing and isolating can be carried out by any suitable technique. For example target molecules can be physisorbed onto a surface, chemisorbed (covalent or non-covalent) onto a surface, or presented in a lipid bilayer on a surface. Moreover, targets can be presented in the cell membrane of live or dead cells. Beads can be exposed to the targets by flowing them over the targets in solution. A wash of unbound targets, and drying step are optional. A bound bead can be visualized via optical microscopy, or AFM. The bead can be extracted, in solution or in buffer, via spearing with the AFM tip, via physiosorption onto the AFM tip, via melting onto the AFM (using heat or current through the AFM tip) via electrostatic attraction to the AFM tip, or via suction onto a micropipette tip. The bead will then be removed from the sampling area by retracting the AFM tip or the micropipette tip The subject matter further relates to a method for producing one-bead-one-sequence composition, which comprises the step of hybridizing a microscopic-bead-bound sequenceable molecule to a tag sequence that uniquely identifies and is operably connected to a candidate chemical.

In a preferred embodiment, the hybridization of said tag sequence and said microscopic-bead-bound sequenceable molecule occurs only under highly stringent conditions.

In some embodiments, either the sequencable molecules or the tag sequences are rationally designed to enhance the capture of candidate chemicals on beads. For example, the codons may be comprised of short nucleotide sequences, much like amino acids are encoded by certain nucleic acid codons. Also, all sequences will be designed to have about the same melting temperature.

Products by Process

The subject matter relates to a composition produced by the process of hybridizing a microscopic-bead-bound sequenceable molecule to a tag sequence that uniquely identifies and is operably connected to a candidate chemical.

Synthesis of the Compositions

The biological molecules may be readily prepared by standard techniques of molecular biology, utilizing techniques known to those of ordinary skill in the art and in part as described in greater detail herein.

Products and intermediates may be isolated or purified using one or more standard purification techniques known to one of ordinary skill in the art, including, for example, one or more of simple solvent evaporation, recrystallization, distillation, sublimation, filtration, polymerase chain reaction, Southern blotting, Northern blotting, Western blotting, chromatography, including thin-layer chromatography, affinity chromatography, gel filtration chromatography, ion exchange chromatography, FPLC, HPLC (e.g. reverse phase HPLC), column chromatography, flash chromatography, radial chromatography, trituration, salt precipitation, two-phase separation, polymer precipitation, heat denaturation, isoelectric separation, dialysis, and the like.

The chemical compounds may be readily prepared by standard techniques of organic chemistry, utilizing techniques known to those of ordinary skill in the art and in part as described in greater detail herein.

In the chemical synthesis of chemical compounds and compositions, one skilled in the art will understand that one may need to protect or block various reactive functionalities on the starting compounds or intermediates while a desired reaction is carried out on other portions of the molecule. After the desired reactions are complete, or at any desired time, normally such protecting groups will be removed by, for example, hydrolytic or hydrogenolytic means. Such protection and deprotection steps are conventional in organic chemistry. One skilled in the art is referred to "Protective Groups in Organic Chemistry," McOmie, ed., Plenum Press, New York, N.Y.; and "Protective Groups in Organic Synthesis," Greene, ed., John Wiley & Sons, New York, N.Y. (1981) for the teaching of protective groups which may be useful in the preparation of compounds of the subject matter.

Chemical products and intermediates may be isolated or purified using one or more standard purification techniques, including, for example, one or more of simple solvent evaporation, recrystallization, distillation, sublimation, filtration, chromatography, including thin-layer chromatography, HPLC (e.g. reverse phase HPLC), column chromatography, flash chromatography, radial chromatography, trituration, and the like.

EXAMPLES

The following examples are illustrative of the subject matter and are not intended to be limitations thereon. Unless otherwise indicated, all percentages are based upon 100% by weight of the final composition.

Data Analysis and Interpretation

To predict what kind of data will be obtained from Applicants' experiments, the first question Applicants must answer is "How many small molecule-bead complexes (specific and nonspecific) will bind to the targets on the surface?" It turns out that at any given time there are a few specific molecules bound to the surface for a prolonged time (many seconds), while a few thousand nonspecific molecules are bound transiently (milliseconds). Thus, the challenge is to pick up the specific molecules while filtering out the nonspecific ones. Applicants believe that their approach will address this challenge.

The target area is expected to range in size from $(100\ \mu m)^2$ to several $mm^2$. The flow rate will have to be slow enough so that each small molecule-bead complex has a chance to sample the target area. The diffusion coefficient D of a 10 nm bead (the smallest that Applicants might use, though the method will certainly work for larger beads as well), is approximately equal to $D = k_B T/6\Pi\eta = 4.4\cdot 10^{-11}\ m^2/s$, where $k_B$ is the Boltzmann constant, T is the temperature, $\eta = 10^{-3}$ Pas is the viscosity of water and r is the radius of bead. Thus, on average, it will take a time of $t = <h^2>/6D = 950$ seconds for a 10 nm bead to diffuse through the entire height of the sample drop volume, which is typically about $h = 0.5$ mm. The additional time required for larger beads scales linearly with radius.

With each run, Applicants will analyze a pool of at most $10^9$ small molecule-bead complexes. Out of those $10^9$ molecules Applicants plan to extract the 100 molecules with the highest binding constants. Before automating Applicants' process, 100 molecules are expected to be extracted in a few weeks. With automation, the process will take a few days. The extracted molecules will be sequenced and analyzed for pertinent sequence features.

In the following paragraphs, Applicants present arguments for the feasibility of these objectives based on theoretical considerations. The calculations assume a target area (footprint of target) of $A = \Pi\cdot r^2 = 2.8\cdot 10^{-17}\ m^2$ (r=3 nm) and a TIRF/AFM viewing area about $(100\ \mu m)^2\ 10^{-8}\ m^2$. Thus, there are about $3.5\cdot 10^8$ targets per viewing area. Assuming a sampling height (height of drop) of about 500 μm, Applicants obtain a sampling volume of $10^{-8}$ l and a total target concentration within the sampling volume of $[Tl]_{total} \approx 1.2\ 10^{-8}$ M.

During an experiment a drug candidate (C) binds to a target (T) on the surface. Thus, $$C + T \rightarrow CT$$

At equilibrium, which will be reached after about 15 minutes (see diffusion constant of a 10 nm above), the binding constant of this reaction is $$K = \frac{[CT]}{[CT]\cdot [T]}$$

[CT], [C] and [T] are the concentrations of drug candidate-target complexes, free drug candidate and free target, respectively. Thus, the ratio of bound candidate [CT] to unbound (free in solution) candidate [C] is given by $$\frac{[CT]}{[C]} = K\cdot [T] \qquad (1)$$

As will be seen below, only a tiny fraction of targets have a drug candidate bound while the vast majority of targets are unoccupied. With an error of less than 0.01% Applicants can assume that $[T] \approx [T]_{total} = 1.2\cdot 10^{-9}$ M.

The binding constants of $10^9$ different drug candidates in the pool will range from about $10^9\ M^{-1}$ for specific binders to about $10^2\ M^{-1}$ for totally nonspecific binders. Since the exact distribution of binding constants can not be known for any given pool, Applicants will assume that the binding constants of the drug candidates are inversely proportional to the number of synthetic steps, s, in which a different functional group was added. The "perfect drug" (s=0) has a binding constant of $10^9\ M^{-1}$, while drug candidates that consist of more than 60% different functional groups are considered totally nonspecific and have a binding constant of about $10^2\ M^{-1}$.

A drug candidate synthesized in z steps, each of which adds G functional groups, can have a total of $G^z$ different permutations. One of those $G^z$ permutations is the desired unique drug candidate. All other sequences have one or more differences, s. Using combinatorial theory, the number of drug candidates, P, containing s differences with respect to the "perfect drug" is given by $$P = \binom{z}{s} \cdot (G-1)^s = \frac{z!}{(z-s)! \cdot s!} \cdot (G-1)^s$$

Figure 9:
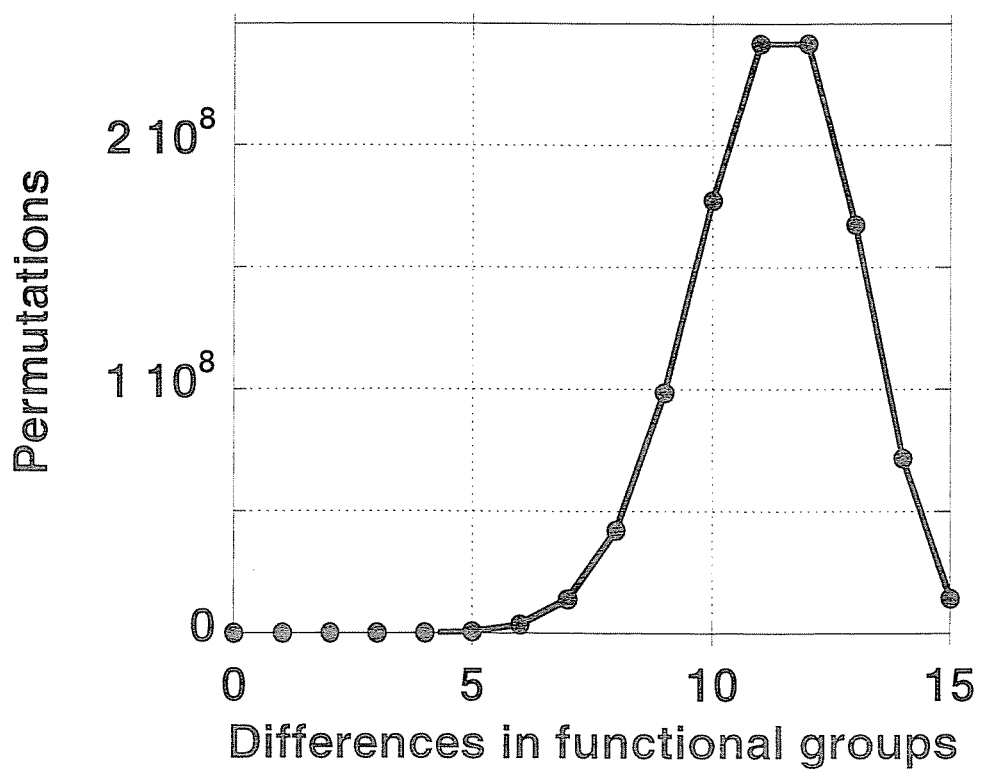
FIG. 9 shows a plot of this function for an oligo of z=15 bases, which, assuming G is on the order of 4, has a total of $G^z=1.07 \cdot 10^9$ different sequences.

FIG. 9 shows a plot of this function for an oligo of z=15 bases, which, assuming G is on the order of 4, has a total of $G^z=1.07 \cdot 10^9$ different sequences.

The binding constant of specific drug candidates, of which there are only a few in the sampling volume, is on the order of $10^9 \, M^{-1}$. Thus, from equation (1) Applicants see that for these drug candidates the ratio of bound vs. unbound (free in solution) is $[CT]/[C]=[T] \cdot K \approx 12$. In practice, this means that specific drug candidates are 12 times more likely to be bound to the target than to be free in solution.

The situation is quite different for nonspecific candidates (oligos). Assuming a pool of $10^9$ drug candidates combinatorially synthesized in z=15 steps ($G^z=1.07 \cdot 10^9$), Applicants consider all molecules that have nine or more different functional groups added at each synthesis step (i.e., they are less than 60% the same) as totally nonspecific. These molecules have a binding constant K on the order of $10^2 \, M^{-1}$ and, using equation (1), Applicants see that $[CT]/[C] \approx 1.2 \cdot 10^{-6}$. Therefore, each totally nonspecific molecule is about $8.3 \cdot 10^5$ times more likely to be in solution than bound to a target. Nevertheless, since there are about $9 \cdot 10^8$ of these molecules in the sampling volume (85% all molecules have nine or more different functional groups), at any given time about 1,100 of them are target-bound-albeit very transiently.

Similar arguments can be made for drug candidates that have intermediate binding constants. In a pool of $10^9$ molecules there are on the order of $5.6 \cdot 10^7$ molecules (5.2% of all molecules) that have 7 or 8 different functional groups and is expected to have a binding constant on the order of $K=10^3 \, M$. From equation (1) Applicants see that $[CT]/[C] \approx 1.2 \cdot 10^{-5}$ and therefore about 670 of those molecules are target-bound while the rest are in solution. Equivalent arguments can be made for the rest of the molecules, so that all in all there are about 3,000 molecules bound to the surface at any given time. Now it can also be seen that the assumption $[T] \approx [T]_{Total}$ is indeed very good, since only about 3,000 out of $10^9$ targets have an candidate bound at any given time.

In summary, it is clear that in order to select the few specific molecules from the few thousand transiently and nonspecifically bound molecules on the surface, a selection mechanism is needed.

As described in this application, Applicants will use the duration, intensity and mobility of the TIRF signals to distinguish the few specific binding events from the nonspecific binding events. Specific binders will have higher intensity, longer duration and less mobility than nonspecific ones. In fact, the threshold of the camera can be adjusted so that it will only detect signals above a certain intensity, which means that signals from nonspecific binders can be filtered out.

In effect, Applicants are using the kinetic nature (dissociation rate) of the small molecule-target binding process in addition to the energetic nature (equilibrium constant) to distinguish specific from nonspecific binding. Thus, though Applicants will pursue subtraction-screening methods to complement the subject matter screening scheme, the kinetic nature of Applicants' screen is expected to prove powerful enough to allow us to directly screen Applicants' bead-conjugated encoded small molecule libraries. Indeed, the subject matter processing of encoded chemical libraries is a promising new tool in the fertile ground of ultra-high-throughput drug discovery.

Example 1

Development of the on-Bead-PCR Methodology

The following example illustrates the preparation of a preferred functionalized bead provided according to the subject matter. Small molecule-bead libraries will be generated by a novel on-bead PCR approach. Thus, Applicants' will use two orthogonal methods to generate monoclonal bead bound DNA polonies.

A. BEAMing PCR.

Figure 5:
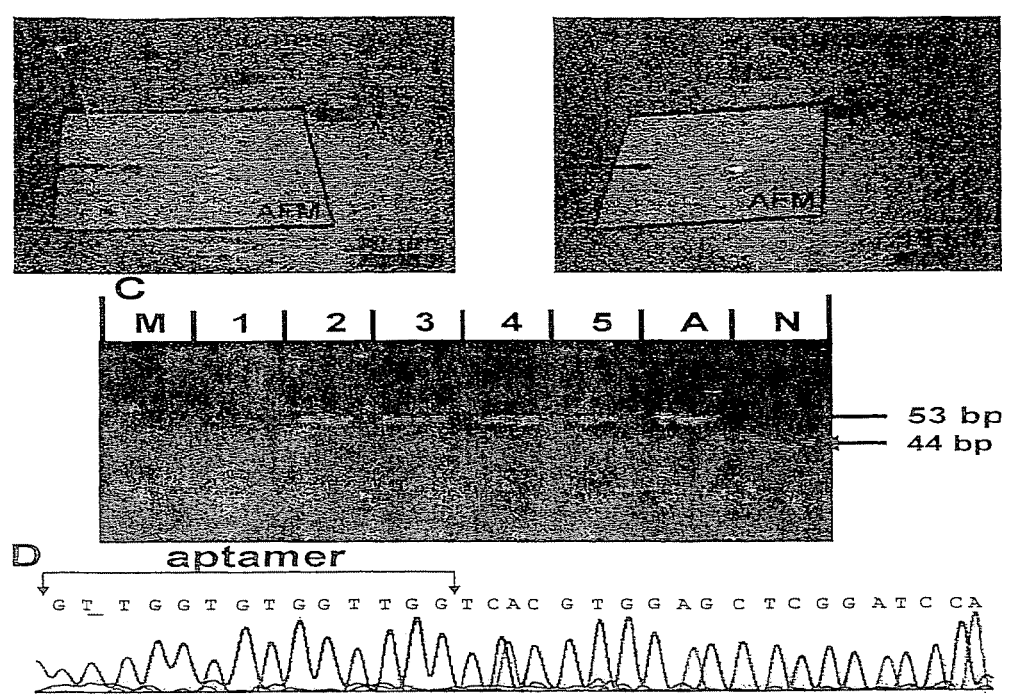
FIG. 5 depicts pick-up of bead and amplification of extracted aptamer. A 1:1 mixture of aptamer-modified beads and nonsense oligo-modified beads was reacted with the thrombin-coated substrate. (A & B) AFM and fluorescence images before (A) and after (B) extraction of a bead. A 30 μm AFM image (small, lighter, semi-transparent square) is overlaid on a section of a larger (specular) fluorescence image; fluorescence light intensity is displayed as height in the underlying fluorescence image. A bead (arrow) was extracted with the AFM tip. The bead is missing in both images after the extraction. (E) 20% PAGE showing the PCR reactions of five extracted beads and corresponding positive (aptamer) and negative (nonsense oligo) controls. All extracted beads are aptamer-modified beads. The aptamer and nonsense fragment are 53 bp and 44 bp, respectively. Lane M, 10 bp marker (lowest band is 30 bp); lane 1-5, PCR reactions of 5 extracted beads; lane A, aptamer control with a PCR reaction of ~100 aptamer molecules; lane N, nonsense control with a PCR reaction of ~100 nonsense molecules. The lower bands in lanes 2-5 and lane A are aborted PCR products. (D) Sequence data for one of the extracted and amplified pieces of DNA. The resulting sequence (SEQ ID NO:10) exactly matches the thrombin aptamer sequence starting at the second G of the aptamer sequence. (The first 20 bases of the 53-base aptamer oligo are missing, since the sequencing facility that we used could not fully sequence such a short fragment.).

"BEAMing" PCR is depicted in FIG. 5. This method derives its name from its four principle components: beads, emulsion, amplification, and magnetics (see, e.g. Dressman, et al., Proceedings of the National Academy of Sciences, 2003, 100(15):8817-8822; Taly, et al., Chembiochem, 2007, 8(3):263-272; and Diehl, et al., Nat Methods, 2006, 3(7):551-9)). To make bead-bound polonies, magnetic beads are conjugated with one PCR primer and are mixed with variable ratios of both PCR primers in the aqueous compartments of an oil-water emulsion. Primers for PCR (red) bound to magnetic beads (cyan), free PCR primers (red and blue), PCR reagents (e.g., polymerase, not shown), and soluble DNA templates (pink, purple, and light blue) are emulsified in mineral oil (green). The resulting aqueous compartments contain one bead and one DNA template strand (center and upper right), or only one of these two (upper left and lower right), or neither (lower left). After thermocycling, the functionalized bead is isolated from other reagents by magnetization. Single-stranded libraries are generated by melting the DNA strands that are not anchored to the bead, separating them from the anchored strands.

B. Bridging PCR.

Figure 6:
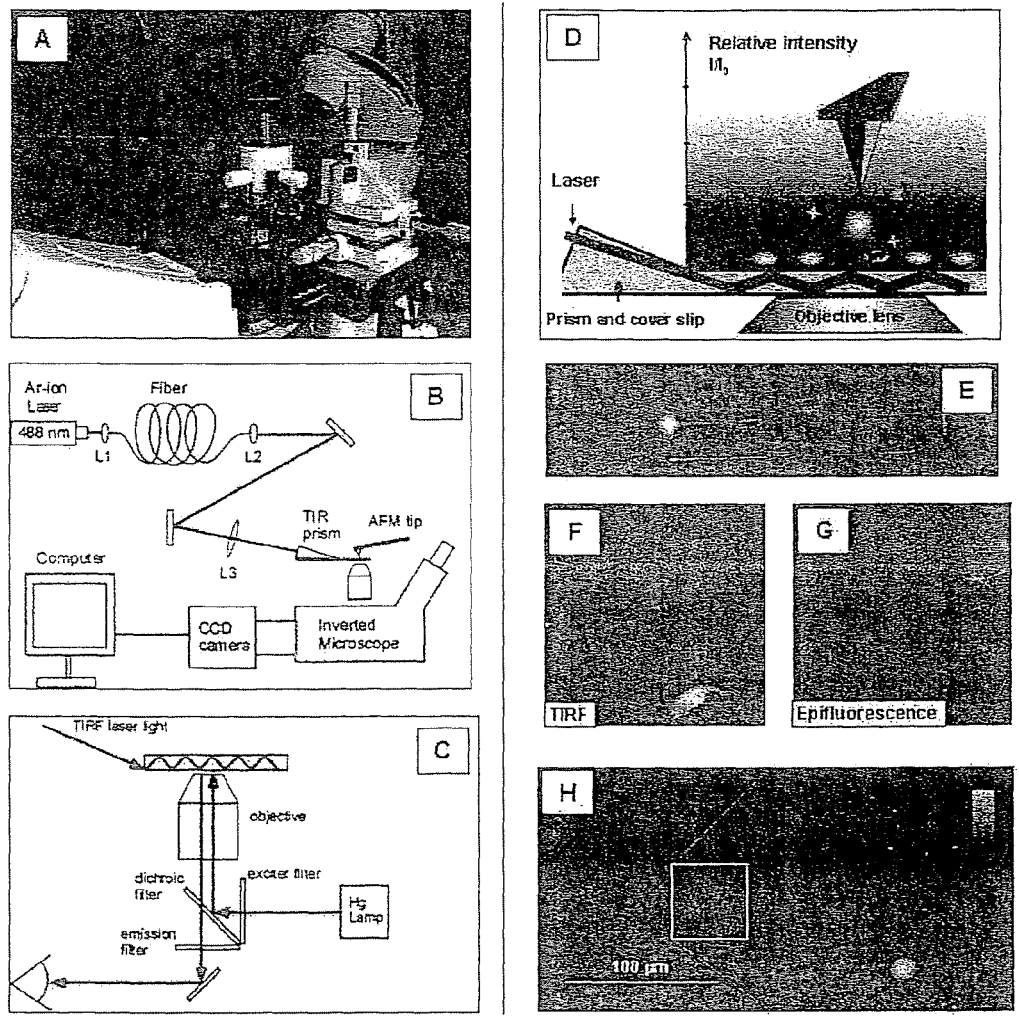
FIG. 6 depicts instrumentation and sample images. (A) Photograph of our hybrid AFM fluorescence microscopy instrument. TIRF illumination is to the left of the AFM, and a stack of x-y-z micrometer screws, which is used to move the sample, is to the right of the AFM. (B) Schematics of the hybrid instrument and (C) the epifluorescence and TIRF light paths. (D) Schematics of TIRF illumination. Laser light is coupled into the cover slip via a prism. The coupled light is totally internally reflected, thus creating an evanescent light field above the substrate. Only molecules on the surface will be illuminated. Target molecules on the substrate, a bead with attached fluorescent aptamers and the AFM tip are shown schematically. (E) Photograph of prism-based TIRF in a cover slip. (F) TIRF image of 200 nm fluorescent beads embedded in 2% agarose solution. Only beads on the surface are illuminated, thus minimizing background from beads in solution. (G) Epifluorescence image of the same region of the same sample (a few seconds later than (F)) All beads (surface and solution) are illuminated, resulting in a large amount of background. (H) Commensurate fluorescence microscopy image (left) and two zoomed-in AFM images of 50 μm and 2 μm size, respectively, of 200 nm beads (Bead appears wider in 2 μm AFM image, because of tip-broadening effect).
Figure 7:
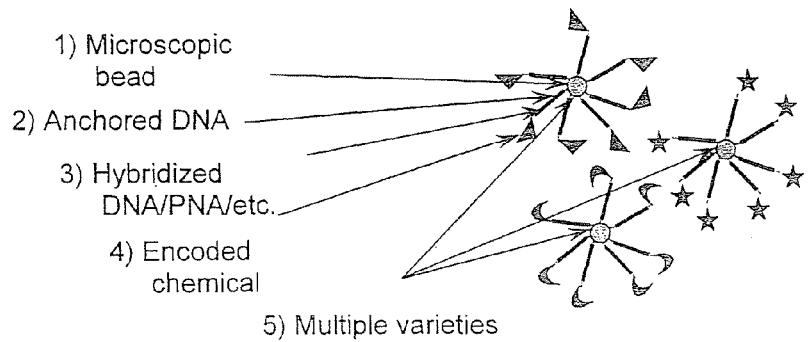
FIG. 7 is a drawing which depicts a composition of the invention.

As shown in FIG. 6, "bridging" PCR, the second technique for generating bead polonies (see, e.g., Bing, et al., Seventh International Symposium on Human Identification, 1996, Genetic Identity Conference Proceedings, found at http://www.promega.com/geneticidproc/ussymp7proc/0726.html; Onodera, et al., Biotechniques, 2002, 32(1):74-6, 78, 80; Pemov, et al., Nucleic Acids Res, 2005, 33(2):e11; and Shapero, et al., Genome Res, 2001, 11(11):1926-1934. In this method, beads are conjugated with both PCR primers, typically via EDC chemistry, but optionally by avidin linkages. Beads (blue) labeled with two types of anchored primers (red and blue) chemically capture one molecule from a ss-DNA library. When a template strand is chemically captured by the bead, the template hybridizes to a bead-bound primer and forms a loop (a "bridge") back to the bead. By thermocycling in the presence of PCR reagents, the template is amplified until all bead-bound primers are elongated. The ss-DNA is allowed to hybridize to its complementary primer and the 1st round of elongation begins. The elongation product is melted, the melted strands hybridize to complementary primers and the 2nd round of elongation begins. Subsequent rounds of PCR cover the bead in identical double stranded loops of DNA. After several rounds of elongation, the anchored primers will all be elongated and the beads will be covered with identical loops of double-stranded (ds) DNA. The resulting dsDNA library can be converted to an ssDNA library via restriction enzymes or cleavable linkers.

It is expected that anchored primers will be shown to function properly for PCR amplification related to bead geometry which is different, and sizes which are significantly smaller, than the 1 mm diameter beads demonstrated in the prior art. To address this, Applicants will validate bridging PCR by covalently linking a small quantity of a known DNA sequence to a large amount of primer-conjugated beads and placed in a standard PCR thermocycler. When the known sequence is amplified, it indicates that the anchored primers and templates are PCR-functional on beads proposed for the subject matter.

BEAMing PCR has been validated using primer-conjugated beads and thermocycling in the presence of a known template, without covalent linkage of the template to the beads. Applicants have amplified templates within the aqueous compartment of a water-in-oil emulsion.

Example 2

Production of a Full Bead Library

A custom-ordered randomer library will be purchased (MWG Biotech, High Point, N.C.), and on-bead-PCR, utilizing bridging PCR, BEAMing PCR, or both, will be used to generate a one-sequence, one-bead library. In the bridging PCR case, restriction enzyme or cleavable linkers, as described above, are expected to convert the dSDNA-bead library into a single-strand DNA library, while BEAMing PCR has been shown to directly produce a ssDNA library. The ssDNA libraries so produced are then used to generate encoded chemical libraries as outlined below.

Example 3

Design and Binding Validation

Applicants have demonstrated that specific binding of chemically defined small molecules to their known targets is detectable when practicing the subject matter. Applicants have hybridized DNA-encoded and PNA-encoded chemicals to their complementary sequences in monoclonal DNA libraries, and then selected against known binding targets.

For example, Applicants have used streptavidin and a FITC-antibody as a target and selected biotin-encoded and FITC-encoded beads from a pool of candidates, as discussed further in Example 4 below.

Alternately, the Applicants have applied the BEAM (beads, emulsion, amplification, magnetics) method to create libraries in a single reaction well. For example, Applicants have taken a 13,824 member DNA library (provided courtesy of Applicants' collaborator, David Liu at Harvard University) and applied the BEAM method to generate a library in which each 1 μm bead displayed multiple copies of the same single stranded DNA sequence.

Avidin magnetic beads (1 um; Chemicell) were conjugated with a 25 base pair biotin oligonucleotide (Integrated DNA Technologies). Through emulsion PCR each bead was coated with thousands of monoclonal DNA sequences from the original Liu library. Preliminary sequencing (Wake Forest Sequencing center) has demonstrated that each bead was displaying a different DNA sequence (data not shown).

Example 4

Detection and Extraction of Target-Bound Beads and Identification of Small Molecules on Beads Applicants expect that the novel integration of i) a one-bead, one sequence library, ii) fluorescence microscopy-aided identification of target bound beads, iii) extraction of attached candidate molecules by a micropipette manipulator, and iiii) identification of target-binding candidate molecules, provides a powerful tool for the discovery of new drug candidates. The following demonstrates selection, extraction and identification of a single molecule from a single bead.

Figure 3:
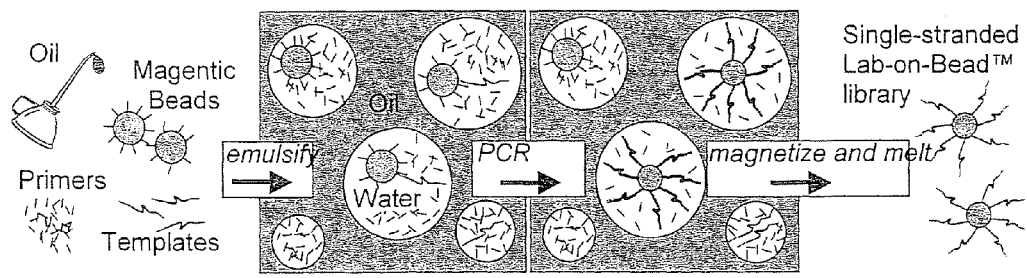
FIG. 3 is a series of drawings which depict "BEAMing" PCR. Primers for PCR (red) bound to magnetic beads (cyan), free PCR primers (red and blue), PCR reagents (e.g., polymerase, not shown), and soluble DNA templates (pink, purple, and light blue) are emulsified in mineral oil (green). The resulting aqueous compartments contain one bead and one DNA template strand (center and upper right), or only one of these two (upper left and lower right), or neither (lower left). After thermocycling, the library is isolated from other reagents by magnetization and DNA strands not anchored to the beads are melted away.
Figure 4:
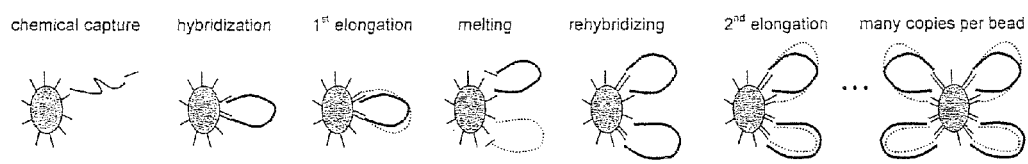
FIG. 4 is a series of drawings which depict "Bridging" PCR. Beads (blue) labeled with two types of anchored primers (red and blue) chemically capture one molecule from a ss-DNA library. The ss-DNA is allowed to hybridize to its complementary primer and the 1st round of elongation begins. The elongation product is melted, the melted strands hybridize to complementary primers and the 2nd round of elongation begins. Subsequent rounds of PCR cover the bead in identical double stranded loops of DNA.

A 1:10 mixture of biotin beads and null beads were reacted with an avidin coated substrate. The biotin beads were the only beads that remained specifically attached to the avidin surface after washing (Gassman et al, supplemental FIG. 3A).

A 17% PAGE gel (data not shown) showed the PCR reactions of twelve extracted beads and corresponding positive (dPNA1) and negative (dNull) controls. All extracted beads were found to be from biotin-dPNA1-modified beads.

A 1:10 mixture of FITC beads and null beads were reacted with an antibody substrate. The FITC beads were the only beads that remained attached to the antibody surface (data not shown).

A 17% PAGE gel (not shown) demonstrated the PCR reactions of ten extracted beads and corresponding positive (dPNA2) and negative (dNull) controls. All extracted beads were shown to be from FITC-dPNA2-modified beads.

A 1:10 mixture of FITC beads to biotin beads were reacted with an antibody surface (data not shown). The FITC beads were the only beads that remained attached to the antibody surface.

A 17% PAGE gel (not shown) revealed the XhoI digested PCR reactions of ten extracted beads and corresponding positive (dPNA2) and negative (dPNA1) controls. All extracted beads are from FITC-dPNA2-modified beads. The PCR primers amplified the positive and negative controls. Thus the DNA was digested with a restriction enzyme for identification. The digest of dPNA 2 yielded a 71 bp fragment and a 38 bp fragment.

Sequence data for two of the extracted and amplified pieces of DNA indicated that the resulting sequence exactly matches the complementary binding sequence for PNA2 (data not shown).

Target molecules, which in this Example are avidin or antibodies, are coated onto glass slides. The fluorescent beads with the attached small molecules are flowed over the target area. High-affinity, target-specific molecules and attached beads bind tightly to the target for relatively prolonged periods. With appropriate stringency conditions, Applicants' methodology have distinguished, selected, and identified target-specific beads to the exclusion of nonspecific beads.

Materials and Methods

PNA and DNA Sequences.

Biotin and fluorescein isothiocyanate (FITC) conjugated PNAs were a kind gift from Nicholas Winssinger (Pianowski and Winssinger, 2008) from his PNA encoded chemical library. PNA 1: biotin-TGATGACGAACGG (N- to C-terminal, SEQ ID NO:1) and PNA 2: FITC-CAAATGAGCAGCC (N- to C-terminal, SEQ ID NO:2). Two 107 nucleotide (nt) single strand DNA sequences containing a complementary binding region to one of these PNAs, and an additional 92 nt DNA sequence containing no PNA binding region were synthesized: dPNA1 (SEQ ID NO:3); dPNA2 (SEQ ID NO:4); and dNull (SEQ ID NO:5) (Table 1, Bioneer). Each DNA was composed of three critical regions: (i) a 5'-NH$_2$ bead linker region, (ii) two 29 nt polymerase chain reaction (PCR) handles (Table 1, italics), and (iii) a PNA binding (capture) region (Table 1, underlined). Additionally, for these experiments, a unique restriction site was added to each sequence for more rapid identification of the sequences identity, BamHI for dPNA1 and XhoI for dPNA2.

TABLE 1

Lab-on-Bead DNA sequences

| Name | Sequence |
|------|----------|
| dPNA1 | 5'-NH$_2$-*TCCCGCGAAATTAATACGACCATGTTATGATA GTCACAGTTTAAC*CCGTTCGTCATCAAT*GTTGGTTACGG ATCCACAGTTAAT-TCAGATAGCTGCAGAGCTCCAGC* |
| dPNA2 | 5'-NH$_2$-*TCCCGCGAAATTAATACGACCATGTTATGATA GTCACAGTTTAAC*CCGTGCTCATTTGA*TGTTGGTTACCT CGAGACAGTTAA-TTCAGATAGCTGCAGAGCTCCAGC* |
| dNull | 5'-NH$_2$-*TCCCGCGAAATTAATACGACCATGTTATGATA GTCACAGTTTAAGTCGACTTTTTACGATACAGTTAATTC AGATAGCTGCAGA-GCTCCAGC* |

Italic-capture PCR handles; underlined-PNA capture region.

Formation of Bead Libraries.

Both yellow green and yellow orange Fluoresbrite1 Carboxylate Microspheres (1 mm, Polysciences) were conjugated with the single strand DNA sequences by 1-ethyl-3-(3-dimethylaminopropyl)-carbodiimide (EDC) coupling similar to Iannone et al., Cytometry 39: 131-140 (2000). Briefly, 2 uL of the bead slurry was washed in 100 uL of 0.1M 2-morpholino-ethanesulfonic acids (MES) pH 4.5, centrifuged for 3 min at 10 000_g, then resuspended again in 50 uL of 0.1M MES. Then, 1 mL of 100 u DNA solution was added to the tube and vortexed briefly. Finally, 10 uL of 50 mg/mL EDC solution was added, vortexed briefly, and incubated at room temperature in the dark for at least 2 h. After incubation, the DNA-bead solution was centrifuged and the supernatant was carefully removed, and the beads were washed three times with 1 mL of PBS (10 mM NaH$_2$PO$_4$, 150 mM NaCl), 0.02% TWEEN® 20, pH 7.2. After the final wash, the beads were resuspended in 50 uL of PBS and stored at 48° C. Final bead suspension was counted with a counting chamber and stored for no longer than a month.

Flow Cells and Surfaces.

Sample chambers were prepared and cleaned as described in Joo and Ha, in Single-Molecule Techniques: A Laboratory Manual, pgs 3-36 (P. Selvin and T. Ha Eds., 2008). Two 0.75 mm diameter holes were drilled into a glass slide to form an inlet and outlet port. Glass slides were sonicated in 10% alconox, acetone, then 1M KOH, while coverslips were sonciated in 1M KOH. Both were washed with copious amount of water and dried with N2. Removable doublesided tape or parafilm was used to seal the chamber. Vacuum was applied to the outlet port to remove solution from the chamber. For the selection of biotin-PNA, about 20 uL of 1 mg/mL of biotinylated BSA in 10 mM Tris-HCl pH 8.0 and 50 mM NaCl (T50) was added into the inject port and incubated for 5 min. The chamber was then washed with 100 mL of T50 buffer, then about 20 mL of 0.4 mg/ml, neutravidin in T50 was added to the chamber and incubated for 2 min. The neutravdin solution was washed from the chamber with 100 ml of T50. For the selection of FITC-PNA, about 20 uL of 1 mg/mL of anti-FITC antibody (Pierce) in PBS was added into the inject port and incubated for 5 min. The chamber was then washed with 100 mL of PBS buffer.

PNA Hybridization.

On the day of the experiment, a 10 mL aliquot of bead suspension, containing about 2×10$^6$ beads, was centrifuged for 3 min at 10,000×g, and the supernatant was carefully removed. Beads were resuspended in 20 uL of 10 mM NaH$_2$PO$_4$, pH 7.2. To this suspension, 1 uL of 100 uM PNA in 10 mM NaH$_2$PO$_4$, pH 7.2 was added and vortexed briefly. The PNA-bead suspension was incubated at 42° C. for 30 min then centrifuged for 3 min at 10,000×g and the supernatant was carefully removed. This bead pellet was then washed three times in the same PBS solution used above, and then resuspended in 10 mL of PBS. In addition to the specific PNA-DNA reaction, beads coated with nonbinding DNA strand, dNull, were also incubated with either the PNA1 or PNA2 sequence, as above. All bead solutions were sonicated prior to selection to reduce aggregation.

Selection of PNA/DNA Beads.

After PNA hybridization and sonication, three types of selection solutions are prepared: (1) with 1 mL of positive binding beads, PNA1-hybridized dPNA1 beads, and 10 µL of nonbinding, PNA1-hybridized dNull beads, for selection off neutravidin surfaces, (2) with 1 uL of positive binding beads, PNA2-hybridized dPNA2 beads, and 10 uL of nonbinding PNA2-hybridized dNull beads, for selection off anti-FITC antibody surfaces, and (3) with 1 uL of positive binding beads, PNA2-hybridized dPNA2 beads, and 10 uL of nonbinding, PNA1-hybridized dPNA1 beads, for selection off anti-FITC antibody surfaces.

The selection solution was added to the washed sample chambers and incubated for 1-2 min. The beads were then removed from the sample chamber and washed with 400 uL of T50 for the neutravidin surfaces or 800 uL of PBS for the anti-FITC antibody surfaces. Application of the wash buffer to the inlet port was carefully maintained, such that the solution meniscus was not pulled through the chamber with the vacuum.

During the incubation and washing, the presence of beads and surface binders was verified by fluorescence microscopy with an inverted Nikon Ti—U microscope. Yellow green beads were excited with a xenon lamp with a standard FITC filter set, and the yellow orange beads were also excited by the xenon lamp with a standard Cy3 filter set. Images were acquired with a Hamamatsu digital camera.

Micropipette Micromanipulator Pick Up of Surface-Bound Beads.

The micropipette tip size must be matched to the diameter of the beadsthat the user was attempting to pick up.

Pipette tip sizes were modified by the pipette pulling procedure, by the type of heating filament in the pipette puller, and by the size of the capillary tubes used as the base material for themicropipettes. Here, a Sutter P-87 micropipette puller with a 1.5 mm×2.0 mm box filament, with borosilicate glass capillaries (Sutter) with an outer diameter of 1 mm and an inner diameter of 0.5 mm was used. The following pipette puller settings were used: Heat-ramp (461), pull=0, time=200, pressure=300, velocity=40 for the pull and 74 for the second.

Tip diameters can be confirmed by imaging the tips in a scanning electron microscope, or by performing a bubble test. Bubble tests are carried out by inserting a pipette into methanol in a glass container, and then applying pressure from a nitrogen gas cylinder, and increasing the back pressure on the pipette until a bubble forms at the tip. Calibrated curves for the tip diameter as a function of the bubble pressure are provided by Sutter Instruments. Here, a pipette tip size of 0.80 um was used.

For pick up, the surface of the microscope slide was brought into focus to identify a bead, then the microscope objective was raised so that the microscope objective was focused at a plane above the target bead. The micropipette tip was then roughly centered over the imaging area by eye, and the tip was lowered toward the target with the manipulator. The pipette was angled at about 20° with respect to the horizontal plane, so the tip was the first part of the pipette to come into contact with the surface. Once the tip was within one or two bead diameters of the bead, a vacuum valve was opened that provides suction at the tip. The bead was then sucked on to the tip by the negative pressure. Once a bead was secured, it can be expelled into a nearby well by the application of positive pressure to the micropipette tip. Alternatively, the pipette tip can be inserted into a microtube and snapped off, insuring the bead has been deposited in the tube.

PCR Amplification of Extracted Beads.

For identification of the bead species selected from the surface, PCR amplification of the DNA sequence conjugated to the bead was required. Given the low number of single-stranded DNA molecules conjugated to the surface, two rounds of PCR, with nested primers, were utilized to provide highly specific amplification of the DNA conjugated to the selected bead. Primer mix 1 (Primer 1 F (SEQ ID NO: 6) and Primer 1 R (SEQ ID NO:7), Table 2) adds an additional 19 bps (base pairs) to the overall length of the DNA (126 bps total, or 128 bps with Taq amplification). The second round of PCR utilizes primer mix 2 (Primer 2 F (SEQ ID NO: 8) and Primer 2 R (SEQ ID NO:9), Table 2), which is 10 bps internal to the previous set and results in a final PCR product of (107 bps, or 109 bps with Taq amplification).

TABLE 2

Lab-on-Bead primer sequences

| Name | Sequence |
| --- | --- |
| Primer 1 F | 5'-GCTATGCATGTCCCGCGAAA |
| Primer 1 R | 5'-CTCGTCACAGCTGGAGCTC |
| Primer 2 F | 5'-TCCCGCGAAATTAATACGACCATGTTATG |
| Primer 2 R | 5'-GCTGGAGCTCTGCAGCTATCTGAATTAAC |

Each single extracted bead was PCR amplified with Ampli-Taq Gold (Applied Biosystems). To each PCR tube containing a single bead was added 1. AmpliTaq Gold reaction buffer, 2 mM $MgCl_2$, 0.2 mM dNTPs, 0.4 mM primer mix 1, 0.25 mL of AmpliTaq Gold. After 25 PCR cycles, with an annealing temperature of 53° C., 1 uL of the PCR product was removed and added to a new PCR tube containing 1×AmpliTaq Gold reaction buffer, 2 mM MgCl2, 0.2 mM dNTPs, 0.4 mM primer mix 2, 0.25 mL of AmpliTaq Gold. It was again subjected to 25 PCR cycles with an annealing temperature of 53° C.

Identification of Surface Binders.

The PCR products from the second round of PCR were run on a 17% native acrylamide gel at 150 V for 1 h and 30 min. The native gel was stained with Sybr Green I nucleic acid stain, and the bands were visualized with a UV transilluminator. If necessary, restriction digest was used to identify similar sized bands. Ten microliters of the second PCR product was digested with XhoI at 37° C. for 16 h. PCR products used for sequencing were gel extracted with the QiaEX II kit (Qiagen) with the second round 2CR primers (Table 2) used as sequencing primers.

Example 5

Detection of Specific Binding Events Using TIRF a. Total internal reflection (TIR) illumination is used to eliminate background noise and improve the signal-to-noise ratio. This technique only illuminates beads that are bound to the surface; beads that are not bound to the surface will not yield a signal. Applicants are using a prism-based set-up, as opposed to objective lens-based set-up, because the former allows control of the incident light angle and thus of the penetration depth. A detected fluorescence signal could come from a specifically bound bead or from a nonspecifically bound bead. Three interrelated characteristics of the fluorescence signal will be used to distinguish specific from nonspecific binding:

Duration. Specifically bound aptamers have a much longer residence time than nonspecifically bound oligos and will thus result in much longer signals. The residence=1/k ($\tau time_d$, where $k_d$ is the dissociation rate) is on the order of 100 seconds for specifically bound aptamers and only about $10^{-4}$ seconds for nonspecifically oligos.

Intensity. Since the intensity of the signal depends on the duration of the surface interaction, specifically bound beads will also emit a more intense fluorescence signal. This is a powerful distinguishing parameter since the detection threshold of the camera can be adjusted to detect only signals of certain intensity and filter out weaker signals. Signals from weakly bound oligos can thus be eliminated.

Mobility. Molecules can diffuse or hop over surfaces with many binding sites. Nonspecifically bound beads have a much higher dissociation rate, and will thus move faster. Consequently, specifically bound beads can be resolved from their nonspecific counterparts by their lower surface mobility.

Figure 8:
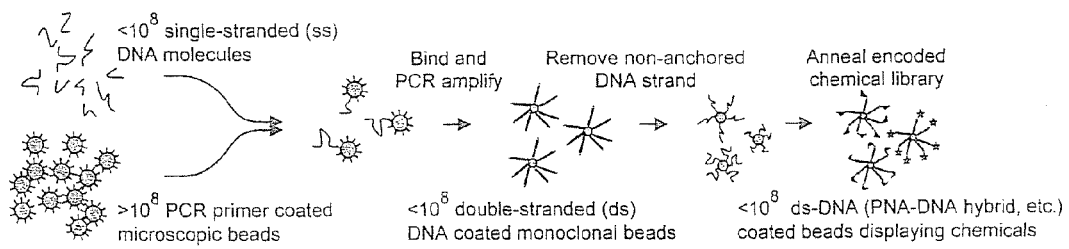
FIG. 8 is a drawing which depicts the process of making a composition of the invention.

FIG. 6 depicts the instrumentation set-up and sample images. FIG. 6A is a photograph of Applicants' hybrid AFM fluorescence microscopy instrument. TIRF illumination is to the left of the AFM, and a stack of x-y-z micrometer screws, which is used to move the sample, is to the right of the AFM. FIG. 8B Schematics of the hybrid instrument and FIG. 8C the epifluorescence and TIRF light paths. FIG. 8D Schematics of TIRF illumination. Laser light is coupled into the cover slip via a prism. The coupled light is totally internally reflected, thus creating an evanescent light field above the substrate. Only molecules on the surface will be illuminated. Target molecules on the substrate, a bead with attached fluorescent aptamers and the AFM tip are shown schematically. FIG. 6E Photograph of prism-based TIRF in a cover slip. FIG. 6F TIRF image of 200 nm fluorescent beads embedded in 2% agarose solution. Only beads on the surface are illuminated, thus minimizing background from beads in solution. FIG. 8G Epifluorescence image of the same region of the same sample (a few seconds later than (F)). All beads (surface and solution) are illuminated, resulting in a large amount of background. FIG. 8H Commensurate fluorescence microscopy image (left) and two zoomed-in AFM images of 50 μm and 2 μm size, respectively, of 200 nm beads. The bead appears wider in 2 μm AFM image, because of tip-broadening effect.

b. Detection and characterization of binding events with the nM-AFM. AFM imaging, combined with force spectroscopy (see c.) will provide additional mechanisms of discrimination between specific and nonspecific binding. After a fluorescence signal has been observed with the optical microscope, the nM-AFM will be used to obtain a high-resolution image of the signal-generating region of the surface. The bead attached to the small molecule is used as a landmark for the aptamer-target binding pair. Overlay. The AFM images and fluorescence images will be overlaid to ensure that the bead that is seen in the AFM image corresponds to the observed fluorescence signal and is thus indicative of a specifically bound bead.

c. Extraction of bead and force spectroscopy. Next, the conditions in the imaging chamber will be changed so that the nM-AFM tip can be used as a "gripper" to retrieve the bead plus the attached aptamer. Manipulating single beads in a controlled manner is carried out in accordance with known techniques as demonstrated in recent work in which Applicants extracted a DNA-coated polystyrene bead and PCR-amplified the attached DNA (Peng et al., Microscopy Research and Technique, 4: 372-81 (2007)). These methods will be further refined so that they can be efficiently automated. Once the tip is connected to the bead, the bead-target binding force, $F_B$, will be determined by force spectroscopy. The magnitude of this force is related to the dissociation rate, $k_d$ as $F_B \propto 1/\ln(k_d)$ and will thus provide a further level of discrimination between specific and nonspecific oligo-target complexes.

d. Small-copy number PCR and sequencing of amplified DNA (identification of small molecule). After extraction, the bead will be eluted off the tip, amplified by single-molecule PCR and sequenced. Applicants have recently shown (Peng et al.) that Applicants can extract 120 nm polystyrene beads coated with a 53 base oligo and amplify the attached DNA via PCR. The quality of the amplified DNA was good enough for sequencing (Peng et al.). The sequence will unequivocally identify the small molecule. The small molecule will then be further analyzed via traditional methods to determine its binding properties (e.g., binding constant, dissociation rate).

e. Optimization of binding, detection and identification protocols for single-bead selection from maximally diverse libraries:

i) Optimize buffers and surface treatment to avoid nonspecific binding, known to be a significant problem in screening and detection applications. There are many ways to reduce nonspecific binding. The most promising seem to be surface functionalization with high-molecular weight polyethylene glycol (5000 MW PEG) or other hydrophilic polymers. An alternative, perhaps easier route is to use Nexterion's slide H. This slide is coated with a thin hydrogel that, according to the company webpage, is the best in preventing nonspecific binding of proteins and DNA. Moreover, any protein of choice is expected to be linked covalently to the hydrogel via easy amine chemistry. Since the hydrogel is only about 20 nm thick, TIRF will still work.

ii) Optimize type and size of beads for ideal imaging and pick-up conditions. Applicants will initially work with carboxylated latex (polystyrene) beads, since they can be to easily functionalized and Applicants have shown that Applicants can extract these beads by simply spearing them with the AFM tip (see FIG. 2 and Peng et al.). Applicants expect to also try gold beads (and thiol chemistry) and/or carboxylated magnetic beads. The beads are expected to be picked up via thiol chemistry or via magnetic AFM tips, respectively. Applicants also envision directly eluting the attached bead into a microfluidics chip that allows immediate PCR-on-a-chip amplification of the attached DNA (bead). The microfluidics chip approach will prevent amplification of beads that may be stuck nonspecifically to the side of the AFM tip.

iii) Initially, Applicants plan to use a pool of known target-specific small molecules. Subsequently, more and more randomized molecules will be added to the pool.

Example 6

Use of the Methodology to Facilitate the Discovery of Lead Compounds

Applicants' ultimate objective involves using therapeutically relevant targets to discover anti-cancer lead compounds and diagnostics. Libraries hybridized to PNA or DNA-tagged compounds will be screened using known or potential cancer targets, such as HER2, a receptor over-expressed in many tumors and the therapeutic target of Herceptin, an antibody-based cancer therapy. Applicants expect that identifying small molecule analogs would reduce the cost of treatment and improve its homogeneity, reliability, production efficiency, and efficacy.

REFERENCES

1. Smith, C. G., J. O'Donnell, and C. G. Smith, The process of new drug discovery and development, p. 117. 2nd ed. 2006, New York: informa Healthcare. 668 p.
2. Sundberg, S. A., High-throughput and ultra-high-throughput screening: solution- and cell-based approaches. Curr Opin Biotechnol, 2000. 11(1): p. 47-53.
3. Gartner, Z. J., et al., DNA-templated organic synthesis and selection of a library of macrocycles. Science, 2004. 305 (5690): p. 1601-5.
4. Harris, J. L. and N. Winssinger, PNA encoding (PNA=peptide nucleic acid): From solution-based libraries to organized microarrays. Chemistry—a European Journal, 2005. 11(23): p. 6792-6801.
5. Haupts, U., M. Rudiger, and A. J. Pope, Macroscopic versus microscopic fluorescence techniques in (ultra)-high-throughput screening. Drug Discovery Today, 2000. 5 (Supplement 1): p. 3-9.
6. Tuerk, C. and L. Gold, Systematic evolution of ligands by exponential enrichment: RNA ligands to bacteriophage T4 DNA polymerase. Science, 1990. 249(4968): p. 505-10.
7. Dressman, D., et al., Transforming single DNA molecules into fluorescent magnetic particles for detection and enumeration of genetic variations. Proceedings of the National Academy of Sciences of the United States of America, 2003. 100(15): p. 8817-8822.
8. Peng, L., et al., A combined atomic force/fluorescence microscopy technique to select aptamers in a single cycle from a small pool of random oligonucleotides. Microsc Res Tech, 2007. 70(4): p. 372-81.
9. Kim, J. B., et al., Polony multiplex analysis of gene expression (PMAGE) in mouse hypertrophic cardiomyopathy. Science, 2007. 316(5830): p. 1481-4.
10. Shendure, J., et al., Accurate multiplex polony sequencing of an evolved bacterial genome. Science, 2005. 309(5741): p. 1728-32.
11. David H. Bing, C. B., Farah N. Rehman, Mark Audeh, Michael Belmarsh, Brian Kelley, and a. C. P. Adams, Bridge Amplification: A Solid Phase PCR System for the Amplification and Detection of Allelic Differences in Single Copy Genes. http://www.promega.com/geneticidproc/ussymp7proc/0726.html, 1996. Seventh International Symposium on Human Identification (Genetic Identity Conference Proceedings).
12. Kohler, G. and C. Milstein, Continuous cultures of fused cells secreting antibody of predefined specificity. Nature, 1975. 256(5517): p. 495-7.
13. Smith, G. P., Filamentous fusion phage: novel expression vectors that display cloned antigens on the virion surface. Science, 1985. 228(4705): p. 1315-7.
14. Walker, M. J. A., T. Barrett, and L. J. Guppy, Functional pharmacology: the drug discovery bottleneck? Drug Discovery Today: TARGETS, 2004. 3(5): p. 208-215.
15. Wright, A. and S. L. Morrison, Antibody variable region glycosylation: biochemical and clinical effects. Springer Semin Immunopathol, 1993. 15(2-3): p. 259-73.

16. Ritzel, R., et al., Pharmacokinetic, insulinotropic, and glucagonostatic properties of GLP-1 [7-36 amide] after subcutaneous injection in healthy volunteers. Dose-response-relationships. Diabetologia, 1995. 38(6): p. 720-5.
17. Roberts, M. J., M. D. Bentley, and J. M. Harris, Chemistry for peptide and protein PEGylation. Adv Drug Deliv Rev, 2002. 54(4): p. 459-76.
18. Woodward, P. W., et al., Improving the design and analysis of high-throughput screening technology comparison experiments using statistical modeling. J Biomol Screen, 2006. 11(1): p. 5-12.
19. Chen, J., et al., A microsphere-based assay for multiplexed single nucleotide polymorphism analysis using single base chain extension. Genome Res, 2000. 10(4): p. 549-57.
20. Nifli, A. P., et al., Comparison of a multiplex, bead-based fluorescent assay and immunofluorescence methods for the detection of ANA and ANCA autoantibodies in human serum. J Immunol Methods, 2006. 311(1-2): p. 189-97.
21. Gartner, Z. J. and D. R. Liu, The generality of DNA-templated synthesis as a basis for evolving non-natural small molecules. J Am Chem Soc, 2001. 123(28): p. 6961-3.
22. Hardiman, G., Ultra-high-throughput sequencing, microarray-based genomic selection and pharmacogenomics. Pharmacogenomics, 2008. 9(1): p. 5-9.
23. Diaz-Mochon, J. J., et al., Combinatorial libraries—from solution to 2D microarrays. Chemical Communications, 2005(11): p. 1384-1386.
24. Urbina, H. D., et al., Self-assembled small-molecule microarrays for protease screening and profiling. Chembiochem, 2006. 7(11): p. 1790-7.
25. Guthold, M., et al., Direct observation of one-dimensional diffusion and transcription by *Escherichia coli* RNA polymerase. Biophys. J., 1999. 77: p. 2284-2294.
26. Guthold, M., et al., Following the assembly of RNA polymerase-DNA complexes in aqueous solutions with the scanning force microscope. Proc. Natl. Acad. Sci. USA, 1994. 91: p. 12927-12931.
27. Guthold, M., et al., Quantitative Manipulation of DNA and Viruses with the nanoManipulator Scanning Force Microscope. Surf. Interf. Analys., 1999. 27(437-443).
28. Guthold, M., et al., Controlled Manipulation of Molecular Samples with the nanoManipulator. IEEE/ASME Transactions on Mechatronics, 2000. 5: p. 189-197.
29. Guthold, M., et al., Investigation and Modification. of Molecular Structures Using the NanoManipulator. J. Mol. Graph. Model., 1999. 17: p. 187-197.
30. Scholl, S., P. Beuzeboc, and P. Pouillart, Targeting HER2 in other tumor types. Ann Oncol., 2001. 12: p. S81-7.
31. Frankel, A. E., et al., Prospects for immunotoxin therapy in cancer. Annu Rev Med, 1986. 37: p. 125-42.
32. Pastan, I., et al., Immunotoxin therapy of cancer. Nat Rev Cancer, 2006. 6(7): p. 559-65.
33. Singhi, A. D., et al., Selection-subtraction approach (SSA): a universal genetic screening technique that enables negative selection. Proc Natl Acad Sci USA, 2004. 101 (25): p. 9327-32.
34. Shak, S., Overview of the trastuzumab (Herceptin) anti-HER2 monoclonal antibody clinical program in HER2-overexpressing metastatic breast cancer. Herceptin Multinational Investigator Study Group. Semin Oncol., 1999. 26: p. 71-7.
35. Slamon, D. J. and G. M. Clark, Amplification of c-erbB-2 and aggressive human breast tumors? Science, 1988. 240 (4860): p. 47 1795-8.
36. Taly, V., B. T. Kelly, and A. D. Griffiths, proplets as Microreactors for High-Throughput Biology. Chembiochem, 2007. 8(3): p. 263-272.
37. Diehl, F., et al., BEAMing: single-molecule PCR on microparticles in water-in-oil emulsions. Nat Methods, 2006. 3(7): p. 551-9.
38. Onodera, K., J. d'Offay, and U. Melcher, Nylon membrane-immobilized PCR for detection of bovine viruses. Biotechniques, 2002.32 (1): p. 74-6, 78, 80.
39. Pemov, A., et al., DNA analysis with multiplex microarray-enhanced PCR. Nucleic Acids Res, 2005. 33(2): p. ell.
40. Shapero, M. H., et al., SNP genotyping by multiplexed solid-phase amplification and fluorescent minisequencing. Genome Res, 2001. 11(11): p. 1926-34.
41. Leary, J. F., Ultra high-speed sorting. Cytometry Part A, 2005. 67A(2): p. 76-85.
42. Carter, P., et al., Humanization of an anti-p185HER2 antibody for human cancer therapy. Proc Natl Acad Sci USA., 1992. 89: p. 4285-9.

The subject matter being thus described, it will be obvious that the same may be modified or varied in many ways. Such modifications and variations are not to be regarded as a departure from the spirit and scope of the subject matter and all such modifications and variations are intended to be included within the scope of the following claims.

We claim:

1. A method for identifying a candidate molecule from a library of tagged chemicals, which comprises the steps of:
   a) probing a target molecule with a library of chemical compositions, wherein each composition in the library comprises:
      i) a microscopic bead;
      ii) a plurality of identical copies of a single-species, sequenceable molecule produced by at least one of BEAMing PCR or bridge amplification, each operably connected to said microscopic bead; and
      iii) a tag sequence comprising DNA, modified DNA or RNA, which tag sequence is complementary to, and is hybridized to, said sequenceable molecule,
      iv) a candidate chemical operably connected to said tag sequence,
      wherein said tag sequence is a unique identifier for its connected candidate chemical;
   b) isolating each composition which binds to said target molecule;
   c) sequencing said sequenceable molecule from each said composition;
   d) identifying, by hybridization under highly stringent conditions, the tag sequence which complements and hybridizes to the identified sequence of said sequenceable molecule; and
   e) identifying, from a database correlating said tag sequence to its connected candidate chemical, the candidate molecule.

2. The method of claim 1, wherein said candidate chemical is produced by template-directed synthesis using said tag sequence as the template.

3. The method of claim 2, wherein said tag sequence is DNA.

4. The method of claim 2, wherein said tag sequence is operably connected to said candidate chemical by a covalent bond.

5. The method of claim 1, wherein said tag sequence is bound to said candidate chemical during or after the synthesis of said candidate chemical,
   provided that said candidate chemical is not produced by template-directed synthesis using said tag sequence as the template.

6. The method of claim 5, wherein said tag sequence is DNA.

7. The method of claim 5, wherein said tag sequence is operably connected to said candidate chemical by a covalent bond.

8. The method of claim 1, wherein said hybridization of said tag sequence and said sequenceable molecule occurs only under highly stringent conditions.

9. The method of claim 1, wherein said sequenceable molecule is DNA.

10. The method of claim 1, wherein said sequenceable molecule is operably connected to said microscopic bead by a ligand-binding partner pair.

11. The method of claim 10, wherein said ligand-binding partner pair is biotin and one or more biotin ligands selected from the group consisting of avidin, streptavidin, and neutravidin.

12. The method of claim 1, wherein said sequencing the sequenceable molecule is selected from the group consisting of polymerase chain reaction, reverse-transcriptase polymerase chain reaction, or modified polymerase chain reaction.

13. The method of claim 1, wherein said microscopic bead is between 10 nanometers and 30 microns.

14. The method of claim 13, wherein said microscopic bead is between 100 nanometers and 1 micron.

15. The method of claim 1, wherein said microscopic bead comprises glass, plastic, acrylic copolymers, cellulose, nylon, dextran, latex, or polyacrolein.

16. The method of claim 15, wherein said microscopic bead comprises polystyrene.

17. The method of claim 1, comprising between steps (b) and (c) the additional steps of:
   i) isolating the single-species, sequenceable molecule from each said composition which binds to said target molecule; and
   ii) amplifying said sequenceable molecule.

18. The method of claim 17, wherein said amplifying the sequenceable molecule is polymerase chain reaction.

19. The method of claim 1, wherein said plurality of identical copies of a single-species, sequenceable molecule are produced by BEAMing PCR.

20. The method of claim 19, wherein said tag sequence comprises DNA and said sequenceable molecule comprises DNA.

21. A method for producing a one-bead-one-sequence composition, which comprises the steps of:
   (a) generating a microscopic-bead-bound sequenceable molecule by at least one of BEAMing PCR or bridge amplification;
   (b) hybridizing said microscopic-bead-bound sequenceable molecule to a tag sequence comprising DNA, modified DNA or RNA, which tag sequence uniquely identifies and is covalently connected to a candidate chemical.

22. The method of claim 21, wherein said hybridization of said tag sequence and said microscopic-bead-bound sequenceable molecule occurs only under highly stringent conditions.

23. The method of claim 22, wherein:
   said tag sequence is operably connected to said candidate chemical by a covalent bond; and
   said sequenceable molecule is selected from the group consisting of DNA, modified DNA, and RNA.

24. The method of claim 23, wherein said microscopic bead is magnetic.

25. The method of claim 21, wherein said generating step is carried out by BEAMing PCR.

26. The method of claim 25, wherein said tag sequence comprises DNA and said sequenceable molecule comprises DNA.

27. A method for identifying a candidate molecule from a library of tagged chemicals, which comprises the steps of:
   a) probing a target molecule with a library of chemical compositions, wherein each composition in the library comprises:
      i) a microscopic bead;
      ii) a plurality of identical copies of a single-species, DNA sequenceable molecule produced by at least one of BEAMing PCR or bridge amplification, each operably connected to said microscopic bead by a ligand-binding partner pair; and
      iii) a tag sequence comprising DNA, modified DNA or RNA, which tag sequence is complementary to, and is hybridized to, said sequenceable molecule,
      iv) a candidate chemical operably connected to said tag sequence by covalent bond, wherein said candidate chemical is produced by template-directed synthesis using said tag sequence as the template, and wherein said tag sequence is a unique identifier for its connected candidate chemical;
   b) isolating each composition which binds to said target molecule;
   c) isolating the single-species, sequenceable molecule from each said composition which binds to said target molecule; and
   d) amplifying by polymerase chain reaction said sequenceable molecule;
   e) sequencing by polymerase chain reaction said sequenceable molecule from each said composition;
   f) identifying, by hybridization under highly stringent conditions, the tag sequence which complements and hybridizes to the identified sequence of said sequenceable molecule; and
   g) identifying, from a database correlating said tag sequence and its connected candidate chemical, the candidate molecule.

28. The method of claim 27, wherein said plurality of identical copies of a single-species, sequenceable molecule are produced by BEAMing PCR.

29. The method of claim 28, wherein said tag sequence comprises DNA and said sequenceable molecule comprises DNA.

* * * * *

UNITED STATES PATENT AND TRADEMARK OFFICE
CERTIFICATE OF CORRECTION

PATENT NO.      : 8,741,558 B2  
APPLICATION NO. : 13/143433  
DATED           : June 3, 2014  
INVENTOR(S)     : Guthold et al.

Page 1 of 1

It is certified that error appears in the above-identified patent and that said Letters Patent is hereby corrected as shown below:

In the Specification:

Column 10, Line 25: Please correct "of about 10 compared"
to read -- of about $10^{-20}$ M compared --

Column 16, Line 52: Please correct "=1.2·$10^{-9}$ M."
to read -- =1.2·$10^{-8}$ M. --

Column 17, Line 38: Please correct "K=$10^3$ M."
to read -- K=$10^3$ $M^{-1}$. --

Signed and Sealed this  
Seventeenth Day of February, 2015

Michelle K. Lee  
*Deputy Director of the United States Patent and Trademark Office*

SEQUENCE LISTING

```
<160> NUMBER OF SEQ ID NOS: 10

<210> SEQ ID NO 1
<211> LENGTH: 13
<212> TYPE: DNA
<213> ORGANISM: Artificial
<220> FEATURE:
<223> OTHER INFORMATION: Base sequence for biotin conjugated PNA
<220> FEATURE:
<221> NAME/KEY: misc_feature
<222> LOCATION: (1)..(1)
<223> OTHER INFORMATION: Biotin conjugated N-terminal

<400> SEQUENCE: 1
tgatgacgaa cgg                                                          13

<210> SEQ ID NO 2
```

```
<211> LENGTH: 13
<212> TYPE: DNA
<213> ORGANISM: Artificial
<220> FEATURE:
<223> OTHER INFORMATION: Base sequence for FITC conjugated PNA
<220> FEATURE:
<221> NAME/KEY: misc_feature
<222> LOCATION: (1)..(1)
<223> OTHER INFORMATION: FITC conjugated N-terminal

<400> SEQUENCE: 2
caaatgagca gcc                                                           13

<210> SEQ ID NO 3
<211> LENGTH: 107
<212> TYPE: DNA
<213> ORGANISM: Artificial
<220> FEATURE:
<223> OTHER INFORMATION: Lab-on-Bead DNA sequence

<400> SEQUENCE: 3
tcccgcgaaa ttaatacgac catgttatga tagtcacagt ttaacccgtt cgtcatcaat        60
gttggttacg gatccacagt taattcagat agctgcagag ctccagc                    107

<210> SEQ ID NO 4
<211> LENGTH: 107
<212> TYPE: DNA
<213> ORGANISM: Artificial
<220> FEATURE:
<223> OTHER INFORMATION: Lab-on-Bead DNA sequence

<400> SEQUENCE: 4
tcccgcgaaa ttaatacgac catgttatga tagtcacagt ttaacccgtg ctcatttgat        60
gttggttacg gatccacagt taattcagat agctgcagag ctccagc                    107

<210> SEQ ID NO 5
<211> LENGTH: 92
<212> TYPE: DNA
<213> ORGANISM: Artificial
<220> FEATURE:
<223> OTHER INFORMATION: Lab-on-Bead DNA sequence

<400> SEQUENCE: 5
tcccgcgaaa ttaatacgac catgttatga tagtcacagt ttaagtcgac tttttacgat        60
acagttaatt cagatagctg cagagctcca gc                                     92

<210> SEQ ID NO 6
<211> LENGTH: 20
<212> TYPE: DNA
<213> ORGANISM: Artificial
<220> FEATURE:
<223> OTHER INFORMATION: Lab-on-Bead primer sequence

<400> SEQUENCE: 6
gctatgcatg tcccgcgaaa                                                    20

<210> SEQ ID NO 7
<211> LENGTH: 19
<212> TYPE: DNA
<213> ORGANISM: Artificial
<220> FEATURE:
<223> OTHER INFORMATION: Lab-on-Bead primer sequence

<400> SEQUENCE: 7
ctcgtcacag ctggagctc                                                     19
```

```
<210> SEQ ID NO 8
<211> LENGTH: 29
<212> TYPE: DNA
<213> ORGANISM: Artificial
<220> FEATURE:
<223> OTHER INFORMATION: Lab-on-Bead primer sequence

<400> SEQUENCE: 8
tcccgcgaaa ttaatacgac catgttatg                                29

<210> SEQ ID NO 9
<211> LENGTH: 29
<212> TYPE: DNA
<213> ORGANISM: Artificial
<220> FEATURE:
<223> OTHER INFORMATION: Lab-on-Bead primer sequence

<400> SEQUENCE: 9
gctggagctc tgcagctatc tgaattaac                                29

<210> SEQ ID NO 10
<211> LENGTH: 34
<212> TYPE: DNA
<213> ORGANISM: Artificial
<220> FEATURE:
<223> OTHER INFORMATION: PCR amplification product sequence

<400> SEQUENCE: 10
gttggtgtgg ttggtcacgt ggagctcgga tcca                          34
```